(12) United States Patent
Laing et al.

(10) Patent No.: US 11,534,093 B2
(45) Date of Patent: Dec. 27, 2022

(54) TESTING DEVICE FOR A UROFLOWMETER

(71) Applicant: ClearTrac Technologies, LLC, Elizabethton, TN (US)

(72) Inventors: Brent Laing, Greenwood Village, CO (US); John Green, Elizabethton, TN (US); Paul R. Johnson, Boulder, CO (US); Robert John Smith, Louisville, CO (US); Robert Edwin Schneider, Erie, CO (US); Magnus Hargis, Hudson, CO (US); Elise Geolat Edson, Boulder, CO (US); Elizabeth A. O'Brien, Louisville, CO (US)

(73) Assignee: ClearTrac Technologies, LLC, Elizabethton, TN (US)

( * ) Notice: Subject to any disclaimer, the term of this patent is extended or adjusted under 35 U.S.C. 154(b) by 758 days.

(21) Appl. No.: 16/296,647

(22) Filed: Mar. 8, 2019

(65) Prior Publication Data

US 2019/0365306 A1    Dec. 5, 2019

Related U.S. Application Data

(60) Provisional application No. 62/679,582, filed on Jun. 1, 2018.

(51) Int. Cl.
*A61B 5/20*    (2006.01)
*A61B 10/00*    (2006.01)
(Continued)

(52) U.S. Cl.
CPC .............. *A61B 5/208* (2013.01); *A61B 5/205* (2013.01); *A61B 10/007* (2013.01);
(Continued)

(58) Field of Classification Search
CPC .................... B23Q 1/50–585; A61B 5/20–297
See application file for complete search history.

(56) References Cited

U.S. PATENT DOCUMENTS 2,648,981 A    8/1953    Drake
3,172,130 A    3/1965    Lange
(Continued)

FOREIGN PATENT DOCUMENTS

CN    2221776 Y    3/1996
CN    105769223 A    7/2016
(Continued)

OTHER PUBLICATIONS

PCT, "International Search Report and Written Opinion", Application No. PCT/US2019/021292, dated May 8, 2019, 11 pages.
(Continued)

*Primary Examiner* — Justin N Olamit
(74) *Attorney, Agent, or Firm* — Dorsey & Whitney LLP

(57) ABSTRACT

The test lab set-up includes a test flow bench for mounting one or more test devices, an adjustable nozzle for simulating urine flow, and a sensor for collecting data associated with the simulated urine flowing through the test device(s). A computing device for measuring and/or calculating various parameters associated with the simulated urine flow may also be included. The test device may have a shape corresponding to a handheld uroflowmeter subject to testing. The angle of the adjustable nozzle may be adjusted to test for various angles of urine flow. Similarly, the angle, pitch, and roll of the test device may be adjusted to test for various angles at which a uroflowmeter is held. As fluid flows through the test device, the sensor collects information such as, for example, flow rate, duration, volume, and the like. The sensor transmits the data collected to a computing device for additional processing.

15 Claims, 15 Drawing Sheets

(51) Int. Cl.
  *G01F 23/26* (2022.01)
  *G06F 9/54* (2006.01)
  *B23Q 1/54* (2006.01)
  *G01D 21/00* (2006.01)
  *G01M 99/00* (2011.01)
  *A61B 5/00* (2006.01)

(52) U.S. Cl.
  CPC ........... *B23Q 1/5475* (2013.01); *G01D 21/00* (2013.01); *G01F 23/26* (2013.01); *G01M 99/00* (2013.01); *G06F 9/542* (2013.01); *A61B 5/0059* (2013.01); *A61B 5/204* (2013.01); *A61B 5/7275* (2013.01); *A61B 2562/0223* (2013.01)

(56) References Cited

U.S. PATENT DOCUMENTS

| | | |
|---|---|---|
| 3,219,276 A | 11/1965 | Norris |
| 3,859,854 A | 1/1975 | Dye et al. |
| 3,871,230 A | 3/1975 | Dye et al. |
| 3,884,072 A | 5/1975 | Cheng |
| 3,929,412 A | 12/1975 | Villari |
| 3,931,972 A | 1/1976 | Fabian |
| 4,051,431 A | 9/1977 | Wurster |
| 4,085,616 A | 4/1978 | Patel et al. |
| 4,131,016 A | 12/1978 | Layton |
| 4,238,448 A | 12/1980 | Layton et al. |
| 4,343,316 A | 8/1982 | Jespersen |
| 4,554,687 A | 11/1985 | Carter et al. |
| 4,569,090 A | 2/1986 | Muller |
| 4,576,076 A * | 3/1986 | Pyle ............... B23D 45/024 83/486.1 |
| 4,619,273 A | 10/1986 | Iosif |
| D296,360 S | 6/1988 | Oelberg |
| 4,832,046 A | 5/1989 | Parrish |
| 4,891,993 A | 1/1990 | Barker |
| 5,046,510 A * | 9/1991 | Ams ............... A61B 5/208 600/584 |
| 5,062,304 A | 11/1991 | Van et al. |
| 5,176,148 A | 1/1993 | Wiest et al. |
| 5,186,394 A * | 2/1993 | Tsuji ............... B21B 45/0233 239/263.3 |
| D340,768 S | 10/1993 | Jabour |
| 5,377,101 A | 12/1994 | Rollema |
| 5,422,076 A | 6/1995 | Jones |
| D378,129 S | 2/1997 | Wexler et al. |
| 5,794,541 A * | 8/1998 | Hirose ............... B23Q 1/5462 248/371 |
| D422,851 S | 4/2000 | Joergensen |
| D425,365 S | 5/2000 | Chien |
| D436,801 S | 1/2001 | Wonderley |
| 6,398,742 B1 | 6/2002 | Kim |
| D460,328 S | 7/2002 | De et al. |
| D461,105 S | 8/2002 | Law |
| 6,651,259 B1 | 11/2003 | Hartman et al. |
| D492,995 S | 7/2004 | Rue et al. |
| D494,279 S | 8/2004 | Cogan et al. |
| 6,889,563 B2 | 5/2005 | Tomita et al. |
| 6,904,809 B1 | 6/2005 | Aundal |
| 6,931,943 B1 | 8/2005 | Aundal |
| D545,621 S | 7/2007 | Hood |
| D551,032 S | 9/2007 | Lion et al. |
| D552,431 S | 10/2007 | Chou |
| D572,089 S | 7/2008 | Teys et al. |
| 7,416,542 B2 | 8/2008 | Aundal |
| D598,251 S | 8/2009 | Ikoma et al. |
| 7,606,617 B2 | 10/2009 | Wariar |
| 7,739,907 B2 | 6/2010 | Boiarski |
| D619,246 S | 7/2010 | Hazeres |
| 7,762,596 B1 | 7/2010 | Gaydos et al. |
| 7,819,020 B2 | 10/2010 | Jacobi et al. |
| 7,892,217 B2 | 2/2011 | Boiarski |
| 8,141,420 B2 | 3/2012 | Hirao |
| D659,558 S | 5/2012 | Johnson et al. |
| 8,231,552 B2 | 7/2012 | Shahar et al. |
| 8,424,376 B2 | 4/2013 | Boiarski |
| D681,392 S | 5/2013 | Dichraff et al. |
| D688,370 S | 8/2013 | Desai |
| 8,500,705 B2 | 8/2013 | Kim |
| 8,544,341 B2 | 10/2013 | Grumbles et al. |
| 8,574,492 B2 * | 11/2013 | Morita ............... A61L 2/18 134/131 |
| D709,185 S | 7/2014 | Queiroli |
| 8,813,551 B2 | 8/2014 | Boiarski |
| 9,021,878 B2 | 5/2015 | Grinstein et al. |
| D736,043 S | 8/2015 | Lee et al. |
| D770,613 S | 11/2016 | Roberts |
| 9,642,737 B2 | 5/2017 | Seres et al. |
| 9,775,556 B2 | 10/2017 | Dimino et al. |
| 9,885,598 B2 | 2/2018 | Tesar et al. |
| D823,652 S | 7/2018 | Dooley et al. |
| 10,034,659 B2 | 7/2018 | Siller Gonzalez et al. |
| D842,985 S | 3/2019 | Heckerman |
| D862,999 S | 10/2019 | Riedel et al. |
| D871,137 S | 12/2019 | Brouillac |
| D873,995 S | 1/2020 | Laing et al. |
| D876,183 S | 2/2020 | Yee |
| 10,578,196 B2 * | 3/2020 | Haremaki ............... B08B 3/022 |
| D889,918 S | 7/2020 | Hubert |
| D893,947 S | 8/2020 | Pulk |
| D914,204 S | 3/2021 | Roberts |
| D919,798 S | 5/2021 | Laing et al. |
| D920,502 S | 5/2021 | Laing et al. |
| 11,029,239 B2 * | 6/2021 | Littley ............... G01N 15/14 |
| D932,632 S | 10/2021 | Laing et al. |
| D932,633 S | 10/2021 | Laing et al. |
| D932,648 S | 10/2021 | Laing et al. |
| D933,238 S | 10/2021 | Laing et al. |
| D933,239 S | 10/2021 | Laing et al. |
| D933,240 S | 10/2021 | Laing et al. |
| D933,241 S | 10/2021 | Liang et al. |
| 2005/0261605 A1 | 11/2005 | Shemer et al. |
| 2008/0312556 A1 | 12/2008 | Dijkman |
| 2008/0312557 A1 | 12/2008 | Cho et al. |
| 2011/0000309 A1 | 1/2011 | Griffiths et al. |
| 2012/0109008 A1 | 5/2012 | Charlez et al. |
| 2013/0143252 A1 | 6/2013 | Knight et al. |
| 2016/0029942 A1 | 2/2016 | Paulsen et al. |
| 2016/0051176 A1 | 2/2016 | Ramos et al. |
| 2017/0020433 A1 | 1/2017 | Hotaling et al. |
| 2017/0086728 A1 | 3/2017 | Hidas |
| 2017/0105670 A1 | 4/2017 | Holt et al. |
| 2017/0135622 A1 | 5/2017 | Shimokawa et al. |
| 2017/0307423 A1 | 10/2017 | Pahwa et al. |
| 2018/0085008 A1 | 3/2018 | Hall et al. |
| 2018/0303465 A1 | 10/2018 | Lyon et al. |
| 2019/0039201 A1 * | 2/2019 | Müller ............... B23Q 1/623 |
| 2019/0365306 A1 | 12/2019 | Laing et al. |
| 2019/0365307 A1 | 12/2019 | Laing et al. |
| 2019/0365308 A1 | 12/2019 | Laing et al. |
| 2020/0209044 A1 | 7/2020 | Holt et al. |
| 2020/0268303 A1 | 8/2020 | Oliva |

FOREIGN PATENT DOCUMENTS

| | | |
|---|---|---|
| CN | 205494247 U | 8/2016 |
| CN | 106037766 A | 10/2016 |
| DE | 3007855 A1 | 9/1981 |
| DE | 19733630 A1 | 2/1999 |
| DE | 102014008760 A1 | 1/2015 |
| EM | 005840378-0001 | 11/2018 |
| EM | 005840378-0002 | 11/2018 |
| EM | 005840378-0003 | 11/2018 |
| EM | 005840436-0001 | 11/2018 |
| EM | 005840436-0002 | 11/2018 |
| EM | 005840436-0003 | 11/2018 |
| EM | 006821633-001 | 9/2019 |
| EM | 006821633-0002 | 9/2019 |
| EM | 006821633-0003 | 9/2019 |
| EM | 006821633-0004 | 9/2019 |
| EP | 2303124 B1 | 8/2012 |
| EP | 2741671 B1 | 1/2016 |

(56) References Cited

FOREIGN PATENT DOCUMENTS

| | | |
|---|---|---|
| EP | 2716219 B1 | 3/2017 |
| EP | 2564778 B1 | 4/2018 |
| JP | 3729732 B2 | 10/2005 |
| KR | 20110030826 A | 3/2011 |
| KR | 20180036022 A | 4/2018 |
| RU | 2034516 C1 | 5/1995 |
| RU | 2071724 C1 | 1/1997 |
| RU | 2643110 C1 | 1/2018 |
| WO | 9925246 A1 | 5/1999 |
| WO | 2009035599 A1 | 3/2009 |
| WO | 2009142508 A1 | 11/2009 |
| WO | 2014141234 A1 | 9/2014 |
| WO | 2016056571 A1 | 4/2016 |
| WO | 2017036952 A1 | 3/2017 |
| WO | 2017149272 A1 | 9/2017 |
| WO | 2018036664 A1 | 3/2018 |
| WO | 2018051244 A1 | 3/2018 |

OTHER PUBLICATIONS

Extended European Search Report dated Feb. 3, 2022 in connection with European Patent Application No. 19812560.1, 8 pages.

Drive Medical. "Drive Medical Folding Steel Bedside Commode, Grey." obtained Nov. 12, 2018 from <https://www.amazon.com/Drive-Medical-Folding-Bedside-Commode/dp/B001HP7AQE/ref=sr_1_3?s=industrial&ie=UTF8&&qid=1539732631&sr=1-3&keywords=commode>, 8 pages.

Specimen Collection Unit. "Specimen Collection Unit, QTY of 1." obtained Nov. 12, 2018 from <https://www.amazon.com/Specimen-Collection-Unit-QTY-1/dp/B002ZUCVP0#feature-bullets-btf>, 6 pages.

Bestmedical. "Uroflowmeter: Portable & wireless." obtained Nov. 12, 2018 from <http://www.best-medical.nl/uroflowmeter/>, 6 pages., Jan. 1, 2016.

MDTI. "Uflow meter Male Urine Peak Flow Device." obtained Nov. 12, 2018 from <https://www.mdti.co.uk/uflow->, 2 pages., Jan. 1, 2017.

Albyn Medical Product Detail. "SmartFlow: SmartFlow brings together high specifications and ease-of-use." Obtained Nov. 12, 2018 from <http://www.albynmedical.com/products/ProductDetail.aspx?ID=8>, 2 pages., Jan. 1, 2018.

Laborie: "Uroflometry: Uroflowmeters designed for practical, everyday studies, available in a range of configurations to meet different demands." obtained Nov. 12, 2018 from <https://www.laborie.com/category/urology-urogynecology/uroflowmetry/>, 6 pages., Jan. 1, 2018.

Minze Health. "Homeflow." obtained Nov. 12, 2018 from <https://minzehealth.com/products/homeflow/>, 8 pages., Jan. 1, 2018.

Chun, Kwonsoo , et al., Kwonsoo, Chun et al. "Noninvasive Medical Tools for Evaluating Voiding Pattern in Real Life." International Neurology Journal, 2017, S10-16., Jan. 1, 2017.

Do It Yourself , "Urinal Repair: Troubleshoot Urinal Plumbing Problems", https://web.archive.org/web/20171015111849/http://www.doityourself.com/urinal-repair-troubleshoot-urinal-plumbing-problems; accessed on May 13, 2019, Oct. 15, 2017, 3 pages.

PCT , "International Search Report and Written Opinion", Application No. PCT/US19/21421, dated May 31, 2019, 16 pages.

\* cited by examiner

TESTING DEVICE FOR A UROFLOWMETER

CROSS REFERENCE TO RELATED APPLICATIONS

This application claims the benefit of U.S. Provisional Application No. 62/679,582, filed on Jun. 1, 2018 and entitled "Uroflowmeter", the entirety of which is incorporated herein by reference for all purposes.

This application is related to U.S. patent application Ser. No. 16/297,417 filed 8 Mar. 2019 and titled, "Urinary Event Detection, Tracking and Analysis"; and U.S. patent application Ser. No. 16/297,192 filed 8 Mar. 2019 and titled "Uroflowmeter" the entirety of each is incorporated herein by reference for all purposes.

TECHNICAL FIELD

The technology described herein relates generally to handheld uroflowmeters and more specifically to methods and systems for testing and validating handheld uroflowmeters.

BACKGROUND

Urine flow rate or urinary flow rate is the volumetric flow rate of urine during urination. That is, it is a measure of the quantity of urine excreted in a specified period of time and the periodic change in rate of urine flow during that time. Urinary flow rate is measured with uroflowmetry, a type of flowmetry device. For example, a uroflowmeter is a device for recording rates of urine flow over the time of a completed void.

Uroflowmeters generally are used to quantitate obstruction to urine flowing from the bladder. For example, a uroflowmeter can be used by a patient to quantify their urine flow rate, and this data can be used with other relevant data (such as the amount of time elapsed and fluid consumed since the patient's last urination "void") to determine whether urine flow from the bladder is being impeded or obstructed. The urination data and assessment can be used by a medical practitioner to develop a treatment plan for the patient and to objectively quantify responses to therapy.

Despite the availability of uroflowmeters, patients tend to not use these devices for various reasons, such as lack of portability and difficulty in consistently keeping a handwritten record of urination and other related data, known as a voiding diary. Costly, non-portable devices, generally housed in physician's offices, fail to allow for optimal timing of the opportunity to empty a naturally full bladder, producing errant results. There is a need for a uroflowmeter that remedies one or more problems of existing uroflowmeters, or at least provides an alternative thereto. In addition, there is a need for a system of testing and validating such a uroflowmeter.

The information included in this Background section of the specification, including any references cited herein and any description or discussion thereof, is included for technical reference purposes only and is not to be regarded subject matter by which the scope of the invention as defined in the claims is to be bound.

SUMMARY

The technology disclosed herein generally relates to methods and systems to test and validate a uroflowmeter. A test lab system for testing and validating a handheld uroflowmeter is disclosed. In some aspects, the system includes a test flow bench configured to test fluid flow through a test device. The test flow bench includes a support assembly, a frame assembly pivotally coupled to the support assembly and configured to support the test device, an adjustable nozzle coupled to the support assembly and positioned above the frame assembly, and a sensor in fluid communication with the adjustable nozzle.

In some aspects, the support assembly includes a base plate, a back plate orthogonally coupled to the base plate, and two arms coupled to opposing side edges of the base plate. In some aspects, at least one of the two arms defines a tilt control slot for receiving a tilt control knob to pivotally couple the frame assembly to the at least one arm.

In some aspects, the frame assembly comprises a mounting frame pivotally coupled to a support frame.

In some aspects, the back plate includes an adjustable upper portion.

In some aspects, the adjustable nozzle is coupled to the adjustable upper portion.

In some aspects, the adjustable nozzle has a first end and a second end, wherein the first end comprises a removable nozzle head and the second end comprises a reduced diameter relative to the first end. Optionally, the adjustable nozzle is adjustable in at least one of an up/down, side to side or angled direction. In some aspects, movement of the adjustable upper portion in a lateral direction moves the adjustable nozzle in a lateral direction. In some aspects, the adjustable nozzle has an adjustable mounting body with a first end pivotally coupled to a second end. Adjusting the position of the first end of the adjustable mounting body relative to the second end adjusts the angle of the adjustable nozzle. The second end of the adjustable mounting body is coupled to a rod, and the rod is coupled to the support assembly. Movement of the rod relative to the support assembly moves the adjustable nozzle in an axial direction.

In some aspects, the test device is coupled to the frame assembly, and the test device has a shape corresponding to a desired shape for a handheld uroflowmeter.

In some aspects, the test device includes a main body defining a flow chamber, and the flow chamber includes a concave surface defining an outlet with a back wall extending vertically from the concave surface.

In some aspects, the test device includes at least two mounting wings on opposing lateral sides of the main body, and the mounting wings couple the test device to the frame assembly.

In some aspects, the test device is positioned below the adjustable nozzle when the test device is coupled to the frame assembly.

Optionally, the shape of the test device is evaluated to assess its impact on one or more fluid flow parameters of fluid flowing through the test device. In some aspects, the one or more fluid flow parameters includes at least one of fluid flow rate, duration, volume, overflow, splash back, and turbulence.

In some aspects, the adjustable nozzle is coupled to a fluid source, wherein fluid flowing from the fluid source through the adjustable nozzle flows into the flow chamber of the test device. Movement of the adjustable nozzle adjusts a path of fluid flow onto the test device when fluid is pumped through the adjustable nozzle. At least one of an angle, position, or orientation of the fluid flowing into the flow chamber of the test device is adjusted by adjusting at least one of the angle, axial direction, or lateral direction of the adjustable nozzle.

Optionally, the test device is coupled to the frame assembly, the test device has a shape corresponding to a desired shape for a handheld uroflowmeter, and movement of the tilt control knob within the tilt control slot pivots the frame assembly and the test device, moving the test device from a first position to at least a second position.

In some aspects, fluid flowing through the adjustable nozzle strikes a first surface of the test device when the test device is in the first position and a second surface of the test device when the test device is in the second position. The first surface may be located at a position along the back wall of the test device. The second surface may be located at a position on the concave surface of the test device.

In some aspects, the test device is coupled to the mounting frame, and the test device has a shape corresponding to a desired shape for a handheld uroflowmeter. In some aspects, the roll of the mounting frame relative to the support frame alters the roll angle of the test device.

In some aspects, the sensor is configured to detect actual flow rate of fluid flowing through the adjustable nozzle.

In some aspects the system includes a computing device, and the computing device includes a processing component configured to determine fluid flow parameters; store fluid flow parameter data; collect data related to actual fluid flow parameters; and/or compare the collected data to the stored data. The fluid flow parameters include at least one of fluid flow rate, duration, and volume.

In some aspects, the system includes one or more motors in electrical communication with the computing device and configured to control pitch and roll of the frame assembly relative to the support assembly. In some aspects, a first motor controls pitch and a second motor controls roll of the frame assembly.

A method of developing and validating a handheld uroflowmeter test device is disclosed. The method includes mounting a test device to a test flow bench. The test flow bench includes: a support assembly; a frame assembly pivotally coupled to the support assembly; an adjustable nozzle coupled to the support assembly and to a fluid source; and a sensor in fluid communication with the adjustable nozzle. The test flow bench is electrically coupled to a computing device and the test device is configured to test one or more features of a handheld uroflowmeter. The method may further include adjusting the frame assembly, the adjustable nozzle, or both; pumping fluid from the fluid source through the adjustable nozzle to the test device; and monitoring, by the computing device, at least one fluid flow parameter of the fluid flowing through the test device, wherein the at least one fluid flow parameter is detected by the sensor and data related to the at least one fluid flow parameter is transmitted to the computing device.

In some aspects, the one or more features of the handheld uroflowmeter includes at least one of device shape and size, outlet shape and size, one or more surface features, and float shape and positioning within the handheld uroflowmeter.

In some aspects, the at least one fluid flow parameter comprises at least one of fluid flow rate, volume, duration, overflow, turbulence, splash back, and timestamp.

In some aspects, the test device is a plate configured to test a surface feature of the handheld uroflowmeter. The surface feature may be at least one of surface shape, grating, protruding features, and aperture number, size and positioning.

In some aspects, the test device is configured to test dissipating urine stream energy of a surface of the handheld uroflowmeter.

In some aspects, the method optionally includes adjusting the test device based on the at least one detected fluid flow parameter and a desired fluid flow parameter.

An apparatus for developing and validating a handheld uroflowmeter test device is disclosed. The apparatus includes a support assembly; a frame assembly pivotally coupled to the support assembly and configured to support a test device with a structure corresponding to a handheld uroflowmeter shape or a handheld uroflowmeter surface feature; and an adjustable nozzle coupled to the support assembly and positioned above the frame assembly, wherein the adjustable nozzle comprises a body defining a conduit therethrough and an adjustment mechanism for adjusting an angle of the adjustable nozzle relative to the support assembly.

In some aspects, the apparatus may further include a flow sensor in fluid communication with the adjustable nozzle, and a computing device coupled to the apparatus.

In some aspects, the test device is coupled to the frame assembly.

This summary is provided to introduce a selection of concepts in a simplified form that are further described below in the Detailed Description. This summary is not intended to identify key features or essential features of the claimed subject matter, nor is it intended to be used to limit the scope of the claimed subject matter. A more extensive presentation of features, details, utilities, and advantages of the present invention as defined in the claims is provided in the following written description of various embodiments and implementations and illustrated in the accompanying drawings.

DETAILED DESCRIPTION

A handheld uroflowmeter, such as one disclosed in U.S. Provisional Application No. 62/679,582 and further disclosed herein, may be developed and tested with a test lab set-up or system developed specifically for a handheld uroflowmeter. The handheld uroflowmeter of the present disclosure is configured, for example, to be portable and compact, to receive urine flow, to reduce turbulent flow and/or splash back of urine, to inhibit urine overflow, to accommodate variations in positioning and orientation, and/or to collect, measure, and transmit data regarding urine flow rate, duration, volume, timestamp of the void and/or other parameters. To test and validate such functions and develop an optimal handheld uroflowmeter, a test lab set-up of the present disclosure may be used. The test lab set-up may simulate urine flow and apply such simulated urine flow to one or more test devices.

The test lab set-up may include a test flow bench for mounting one or more test devices, an adjustable nozzle for simulating urine flow, a sensor for collecting data associated with the simulated urine flowing through the one or more test devices, and a computing device for measuring and/or calculating various parameters associated with the simulated urine flowing through the one or more test devices. A test device may have a shape corresponding to a handheld uroflowmeter to be tested. Alternatively, the test device may be a plate to test various surface conditions. The test device may be mounted to the test flow bench. Water, to simulate urine, may be pumped through the adjustable nozzle at an angle to the test device. The angle may correspond to a typical angle that urine flows out of a person. The angle of the adjustable nozzle may be adjusted to test for various angles of urine flow. Similarly, the angle, pitch, and roll of the test device may also be adjusted to test for various angles that a handheld uroflowmeter may be held by a user. As water flows through the test device, the sensor collects information related to various parameters, such as, for example, flow rate, duration, volume, and the like. The sensor transmits the data collected to a computing device for additional processing.

Figure 1:
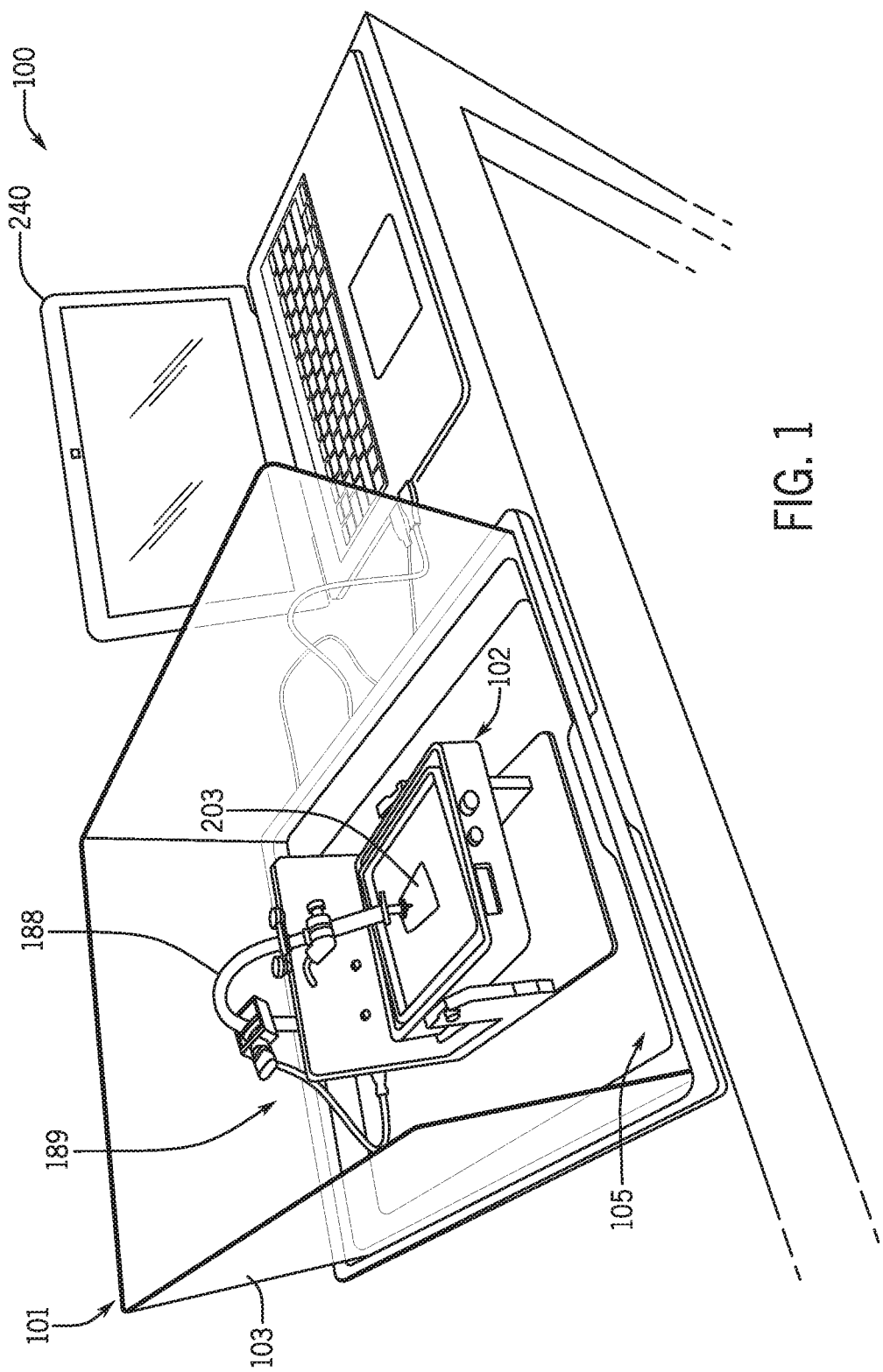
FIG. 1 is a perspective view of a test lab system in accordance with various embodiments of the present disclosure.
Figure 2:
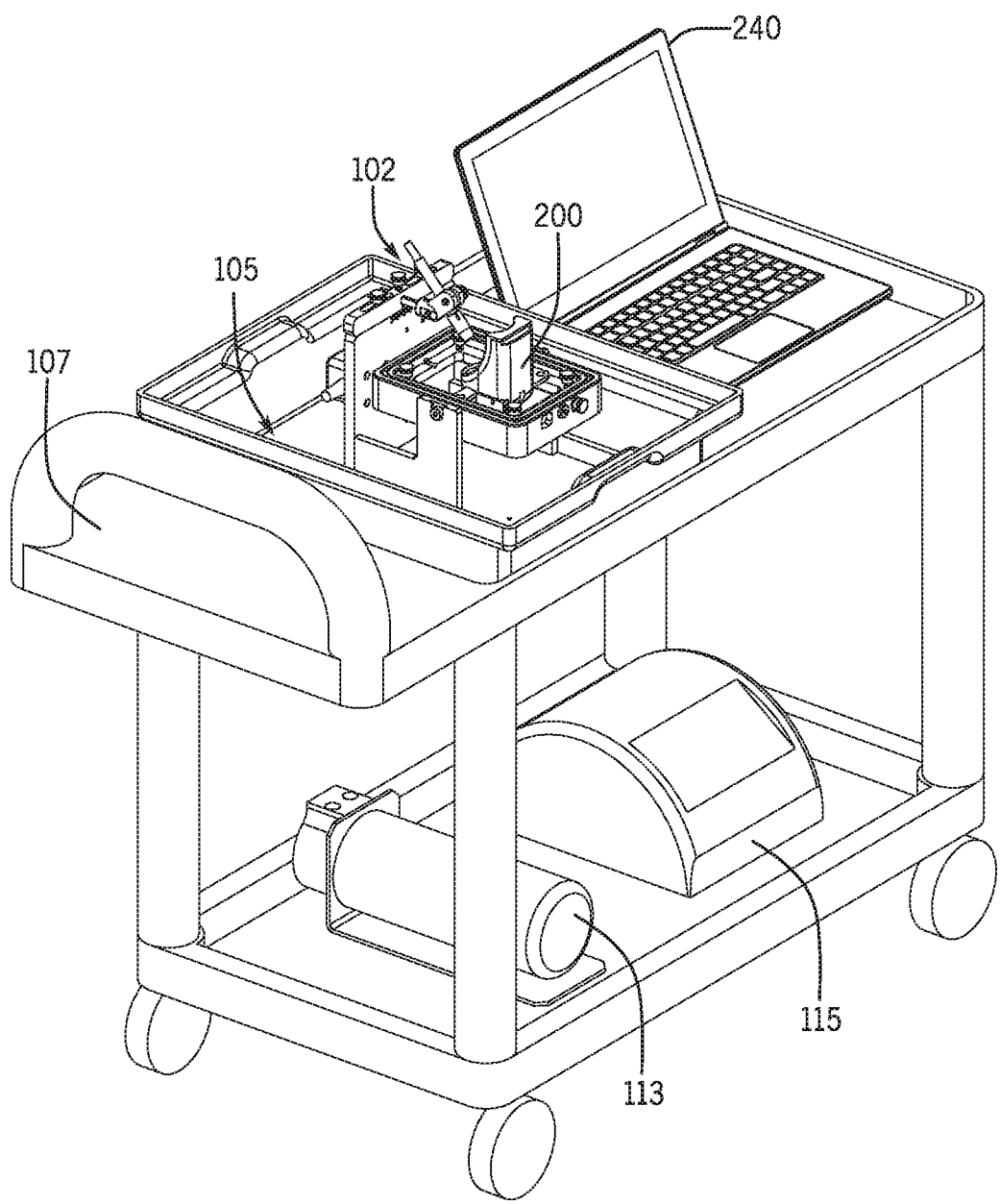
FIG. 2 is a perspective view of a test lab system in accordance with various embodiments of the present disclosure.

Turning to the figures, a system for testing a handheld uroflowmeter of the present disclosure will now be discussed in more detail. FIGS. 1 and 2 illustrate a perspective view of a test lab system 100 in accordance with various embodiments of the present disclosure. The test lab system 100 may include a test flow bench 102, a test housing 101, one or more test devices 200, 203, a pump 113, a pump controller 115, and a computing device 240. The test housing 101 may surround the test flow bench 102 to provide additional protection to a user from any potential fluid splash back or overflow and to provide a place for excess fluid to flow. The test housing 101 may include a base 105 and surrounding walls 103. The base 105 may be a generally rectangular shape with a concave upper surface for receiving the test flow bench 102. The concave upper surface may provide a chamber for excess fluid to flow. The base 105 may include a funnel or outlet coupled to the pump 113 by outflow tubing 189 to allow excess fluid to flow to the pump 113 for reuse in the system 100. Alternatively, the funnel or outlet may be coupled to a fluid collection tank or reservoir for storing the excess fluid. In other embodiments, the base 105 may include a removable filter that may accumulate excess fluid and may be easily removed to allow for easy disposal of the excess fluid. The surrounding walls 103 may act as a splash guard. The surrounding walls 103 may be made of a transparent material, such as glass or plastic, such that a user can still view the test flow bench 102 from any direction. While the test housing 101 is depicted with surrounding walls 103 in the embodiment in FIG. 1, it is contemplated that the surrounding walls 103 may be omitted, as shown in FIG. 2. While the embodiment in FIG. 1 shows the test lab system 100 on a stationary tabletop or surface, the test lab system 100 may also be a moveable system 100. As shown in FIG. 2, for example, the test lab system 100 may be included on a cart 107 or other mobile surface. As shown in FIG. 2, the pump 113 and pump controller 115 may be stored in a convenient location separate from the test flow bench 102, such as, for example, underneath the test flow bench 102. The pump 113 may be any conventional pump for activating and controlling fluid flow. For example, the pump 113 may be a peristaltic pump. The pump 113 may be coupled to the test flow bench 102 by fluid supply tubing 188. For example, the pump 113 may be fluidly connected to the adjustable nozzle 108. The pump controller 115 is in communication with the pump 113 to control various activity parameters of the pump (e.g., on/off function, speed, pressure, temperature, power, and the like). As one example, altering the velocity of fluid flowing through the adjustable nozzle 108 may simulate different urinary system characteristics of users. While only one pump 113 is shown, it is contemplated that multiple pumps may be used, for example, to increase the velocity and volume of fluid flowing through the system 100 and to test a wider range of parameters.

Figure 3:
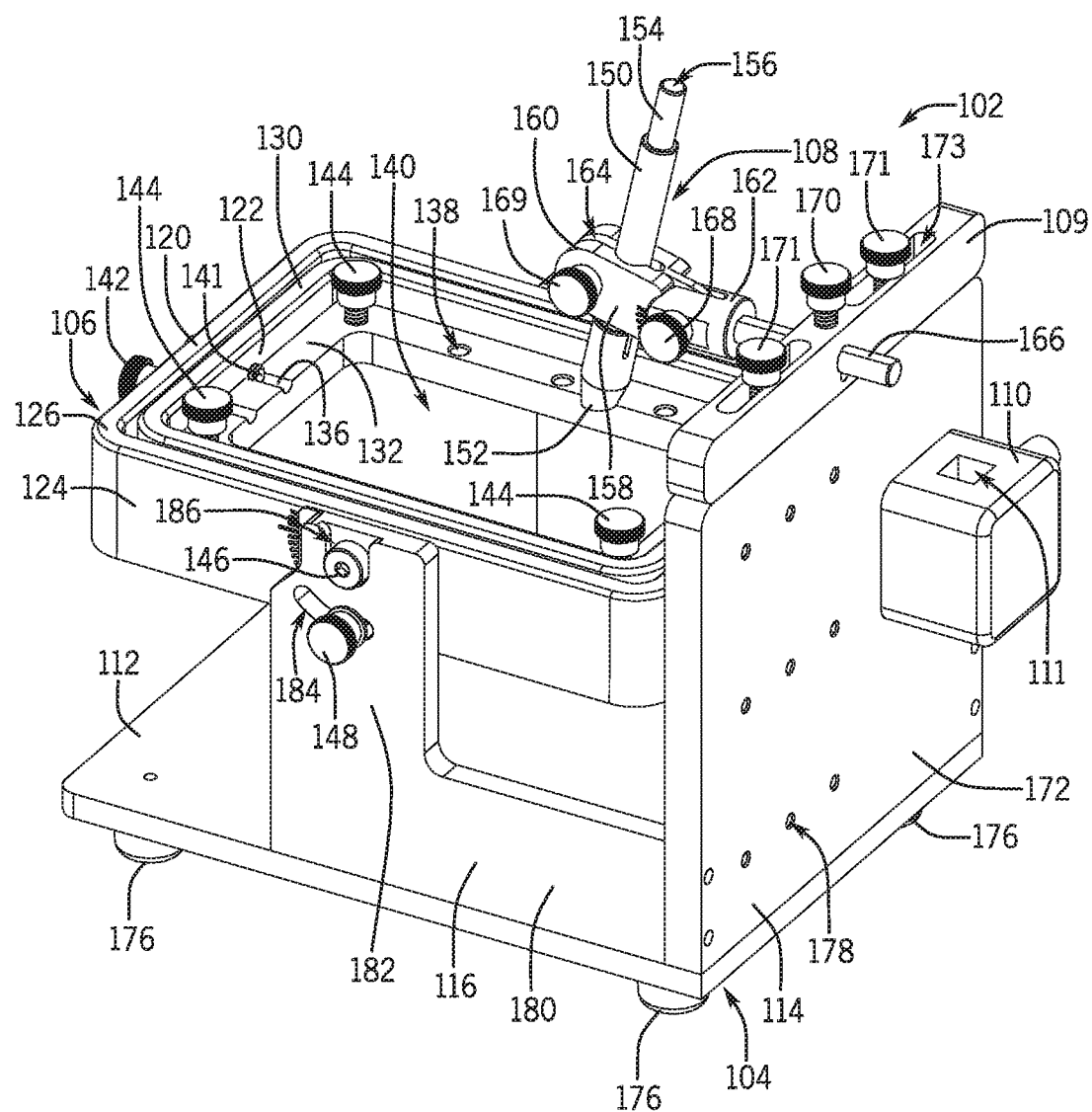
FIG. 3 is a perspective view of a test flow bench of the test lab system of FIGS. 1 and 2.
Figure 8:
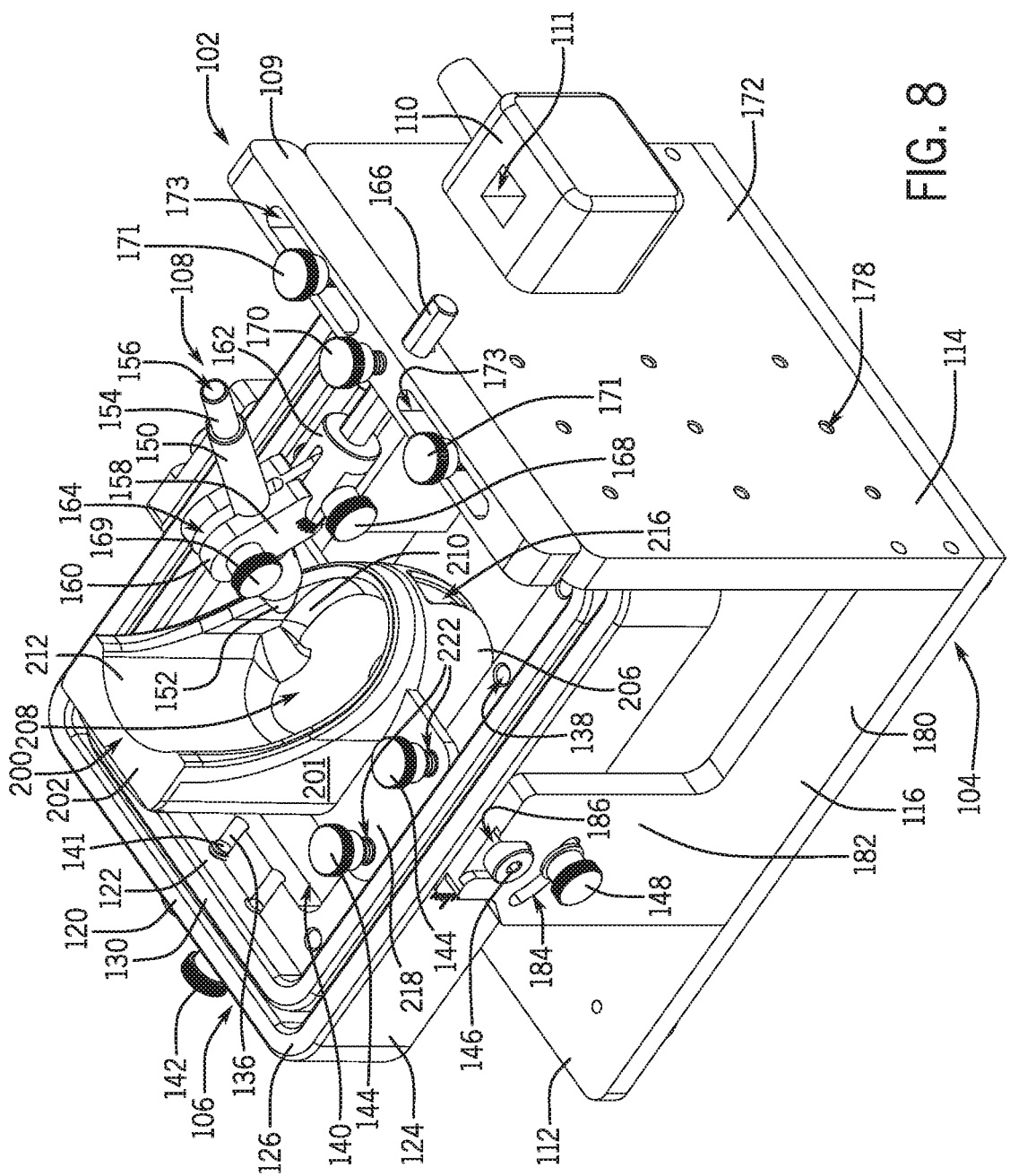
FIG. 8 is a perspective view of the handheld uroflowmeter test device of FIG. 4 mounted to the test flow bench of FIG. 3.
Figure 9:
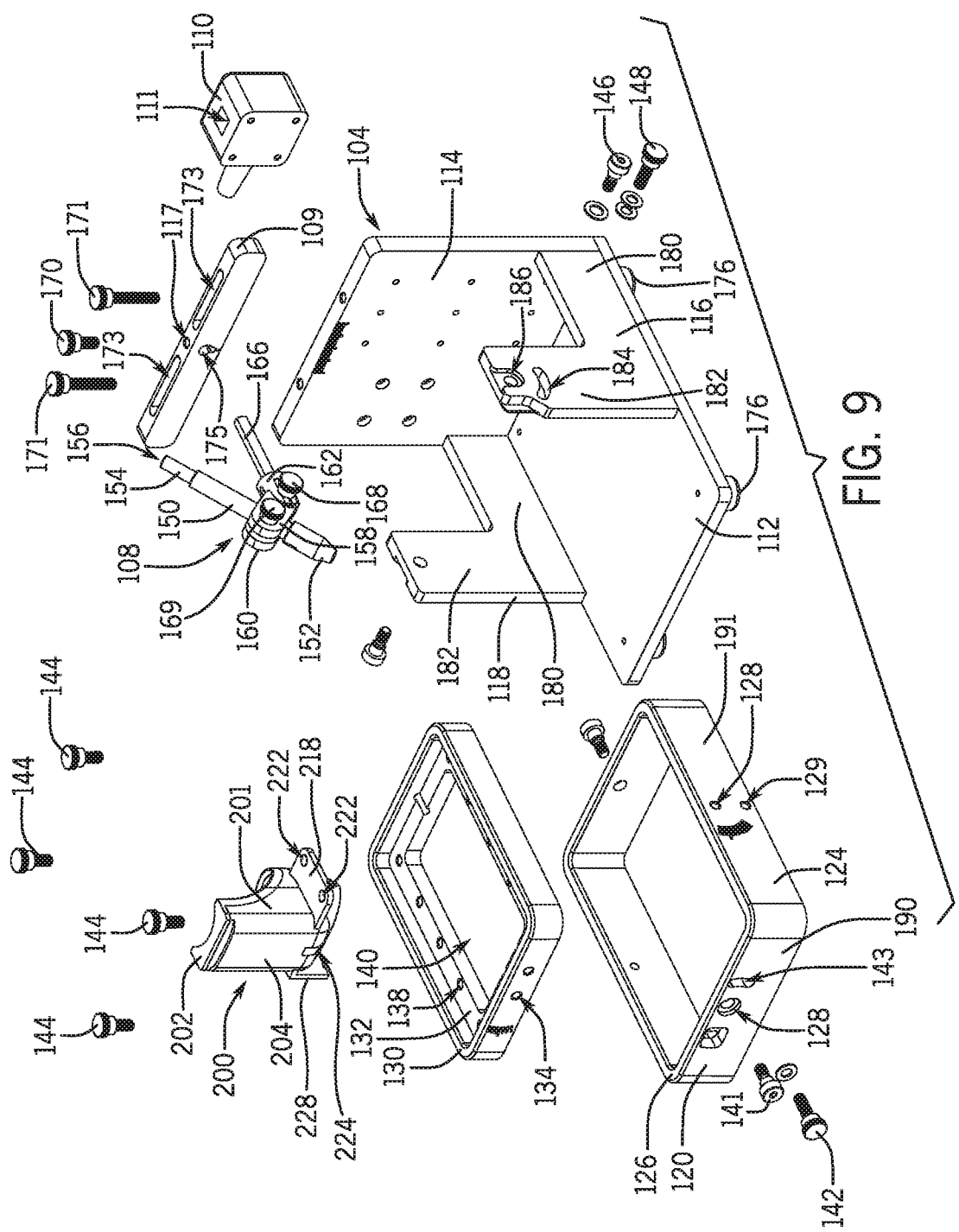
FIG. 9 is an exploded view of the test flow bench and handheld uroflowmeter test device of FIG. 8.

With reference to FIGS. 3, 8 and 9, the test flow bench 102 will now be discussed in more detail. The test flow bench 102 may include a support assembly 104, a frame assembly 106, an adjustable nozzle 108, and a sensor 110. The support assembly 104 may include a base plate 112, a back plate 114, a first arm 116, and a second arm 118. The base plate 112 may have a generally rectangular shape. The base plate 112 may include a plurality of feet 176 on a lower surface to provide additional support to the base plate 112. The feet 176 may raise the base plate 112 above a surface (e.g., a counter or table top). However, it is contemplated that the feet 176 may be omitted and the base plate 112 may be seated directly on the surface. The feet 176 may be made of any supportive material. As one example, the feet 176 are made of the same material as the base plate 112. As another example, the feet 176 are made of rubber. The back plate 114 may also have a generally rectangular shape. The back plate 114 may define a plurality of mounting apertures 178 for mounting various components. For example, the mounting apertures 178 may receive cable/tube tie-downs and the like. The back plate 114 may have an adjustable upper portion 109. The adjustable upper portion 109 may have a nozzle fastening aperture 117 and one or more lateral adjustment slots 173 on an upper surface and a nozzle receiving aperture 175 on a lateral surface. The adjustable upper portion 109 may be coupled to the back plate 114 by one or more fasteners 171. The first and second arms 116, 118 may each have a horizontal portion 180 and a vertical portion 182, forming a bracket or an L-like shape. However, other shapes are contemplated, such as, for example, a generally rectangular shape. An upper portion of the vertical portion 182 may include a tilt or pitch control slot 184 and a fastening aperture 186. The tilt control slot 184 may have a curved shape. For example, the tilt control slot 184 may curve in an upward direction (relative to the base plate 112). The fastening aperture 186 may be defined within the first and second arms 116, 118 above the tilt control slot 184. The fastening aperture 186 defines the pitch axis-of-rotation. It is contemplated that one or both of the first and second arms 116, 118 may include the tilt control slot 184.

The back plate 114 may be mounted on an upper surface of the base plate 112, generally perpendicular to the base plate 112. The back plate 114 may be mounted such that it is flush with an edge of the base plate 112. The first and second arms 116, 118 may be mounted on opposing lateral edges of the base plate 112 and the back plate 114. The first and second arms 116, 118 may be mounted such that the horizontal portion 180 couples to the base plate 112 and back plate 114, while the vertical portion 182 extends upwards, away from the base plate 112. The first and second arms 116, 118 may be perpendicular to both the base plate 112 and the back plate 114. The first and second arms 116, 118 may each have an outer surface that is flush with the opposing lateral edges of the base plate 112 and the back plate 114. In this manner, the support assembly 104 may have four sides defined by the base plate 112, the back plate 114, and the first and second arms 116, 118; however, it is contemplated that the support assembly 104 may have more than four sides.

The frame assembly 106 may be an articulating platform including one or more frames. As shown, the frame assembly 106 may include a support frame or pitch frame 120 and a mounting frame or roll frame 122. The support frame 120 may have a generally rectangular shape with an outer peripheral surface 124 and a top surface 126. As shown in FIG. 9, one or more fastening apertures 128, a knob receiving aperture 129, and a roll control slot 143 may be defined within the support frame 120. As shown, a fastening aperture 128 is positioned centrally along a transverse side 190 of the outer peripheral surface 124, defining a roll axis through the support frame 120, and another fastening aperture 128 is positioned centrally along a longitudinal side 191 of the outer peripheral surface 124, defining a pitch axis through the support frame 120. The mounting frame 122 may also have a generally rectangular shape with an outer frame portion 130 and a mounting surface 132. The outer frame portion 130 may surround the periphery of the mounting surface 132 and may extend upwards from the mounting surface 132. One or more fastening apertures 134 may be defined within the outer frame portion 130. The one or more fastening apertures 134 of the mounting frame 122 may align with the one or more fastening apertures 128 and roll control slot 143 of the support frame 120. One or more fastening slots 136 may be defined within the mounting surface 132. The one or more fastening slots 136 may align with the one or more fastening apertures 134. One or more mounting apertures 138 may also be defined within the mounting surface 132. The mounting frame 122 may have a central opening 140 defined therethrough.

The adjustable nozzle 108 may include a body 150 with a first end 152 and a second end 154 and a cavity 156 defined therethrough. The body 150 may have a generally cylindrical shape. The first end 152 may be tapered. The first end 152 may be a removable nozzle head, such that nozzle heads with different sized and shaped outlets and of rigid or more flexible material may be used to vary the shape and amount of fluid flow therethrough. The second end 154 may be a rigid flow tube with a reduced diameter portion to accept tubing (e.g., the fluid supply tube 188). The adjustable nozzle 108 may include an adjustable mounting body 158. The adjustable mounting body 158 may have a first end 160 pivotally coupled to a second end 162. The first end 160 may have a cavity 164 defined therethrough for receiving the body 150. As one example, the first end 160 is a clamp. The second end 162 may be coupled to a rod 166. The adjustable nozzle 108 may include one or more angle adjustment knobs 168 and one or more axial adjustment knobs 169. For example, as shown, the adjustable nozzle 108 has an axial adjustment knob 169 on the first end 160 of the adjustable mounting body 158 and an angle adjustment knob 168 on the second end 162 of the adjustable mounting body 158.

The sensor 110 may be any sensor capable of detecting various fluid parameters, such as, for example, flow rate (e.g., inflow and outflow rates). As one example, the sensor 110 may be an ultrasonic sensor. In the depicted embodiment, the sensor 110 is a flow meter configured to measure the actual fluid flow rate. The sensor 110 may be calibrated and optimized for a flow rate that is equal to about 0 to 60 ml/sec or between about 15 to 85 ml/sec. The sensor 110 may have an accuracy of about +/−3% (+/−0.12 ml/sec). The sensor 110 may include a tube-receiving aperture 111 for receiving tubing therethrough; however, it is contemplated that the tube-receiving aperture 111 may be omitted. The tubing may be coupled to a fluid source, such that fluid flowing through the tubing flows through the tube-receiving aperture 111 and the flow rate of the fluid flowing therethrough may be measured by the flow meter.

The support frame 120 may be coupled to the support assembly 104. A fastener 146 may extend through the fastening aperture 186 on the first and second arms 116, 118 and into a fastening aperture 128 defined within the support frame 120. A tilt control knob 148 may extend through the tilt control slot 184 on one or both of the first and second arms 116, 118 and may be received within the knob receiving aperture 129 defined within the support frame 120. In this manner, the support frame 120 is suspended above the base plate 112 in between the first and second arms 116, 118. The support frame 120 may be spaced apart from the back plate 114 to allow for rotation of the support frame 120.

The support frame 120 may also be pivotally coupled to the mounting frame 122, forming the frame assembly 106. The mounting frame 122 is positioned within the support frame 120, such that the support frame 120 surrounds the mounting frame 122. One or more fasteners 141 may extend through the fastening apertures 128 defined within the support frame 120 and a roll control knob 142 may extend through the roll control slot 143 defined within the support frame 120, and both may extend through the fastening apertures 134 defined within the mounting frame 122, and seat inside the fastening slots 136 on the mounting surface 132 of the mounting frame 122. One or more fasteners 144 may be positioned within the mounting apertures 138 defined within the mounting frame 122 for securing various test devices, as will be discussed in more detail below. In this manner, the mounting frame 122 is also suspended above the base plate 112 in between the first and second arms 116, 118.

The adjustable nozzle 108 is mounted to an upper portion of the back plate 114. As shown, the rod 166 extends through the nozzle receiving aperture 175 defined within the adjustable upper portion 109 of the back plate 114. A rod fastener 170 may be used to hold the rod 166 and the adjustable nozzle 108 in place. As shown, the rod fastener 170 is placed through the nozzle fastening aperture 117 defined within the upper surface of the adjustable upper portion 109 to secure the rod 166. When mounted, the adjustable nozzle 108 is suspended above the frame assembly 106 and base plate 112. The sensor 110 may be coupled to the back plate 114. As shown, the sensor 110 is coupled to a rear surface 172 of the back plate 114; however, it is contemplated that the sensor 110 may be located elsewhere on the test flow bench 102. The fasteners 141, 144, 146, 170, 171 and the roll and tilt control knobs 142, 148 may be any conventional fastener, such as, for example, screws, bolts, or the like.

It is contemplated that all or some of the components of the test flow bench 102 may be made of plastic. Depending upon the sensor 110 used, plastic may be a suitable material to avoid interference with the sensor 110. However, with some sensors, metal may also be a suitable material. Other materials are also contemplated, such as, for example aluminum alloy, plated steel or stainless steel.

The test flow bench 102 may be coupled to a fluid source, such as, for example the pump 113. As shown in FIG. 1, the adjustable nozzle 108 may be coupled to the fluid source by fluid supply tubing 188. The fluid supply tubing 188 may pass through the tube-receiving aperture 111 in the sensor 110 and may fit securely over the second end 154 of the body 150 of the adjustable nozzle 108 in a manner that is leak proof. In the case in which the sensor 110 does not include the tube-receiving aperture 111, the fluid supply tubing 188 may be coupled adjacent the sensor 110 such that fluid flowing therethrough flows adjacent the sensor 110. The pump 113 may pump fluid stored therein through the fluid supply tubing 188 and to the adjustable nozzle 108. Any fluid with properties similar to urine may be used in the system. For example, the fluid used in the system may be water, saline solution or synthetic urine. Saline solution and synthetic urine may be used to evaluate the effects of dried fluid (such as sticky or crystallized material) on the float pivot and energy-dissipating features.

Figure 5:
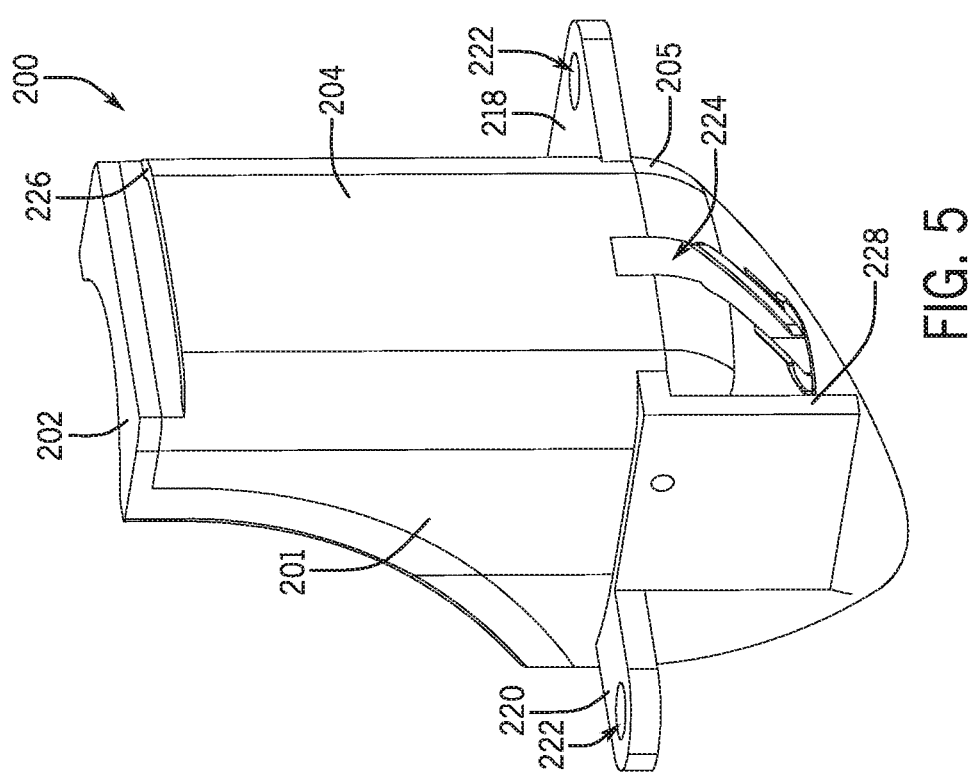
FIG. 5 is a rear view of the handheld uroflowmeter test device of FIG. 4.
Figure 4:
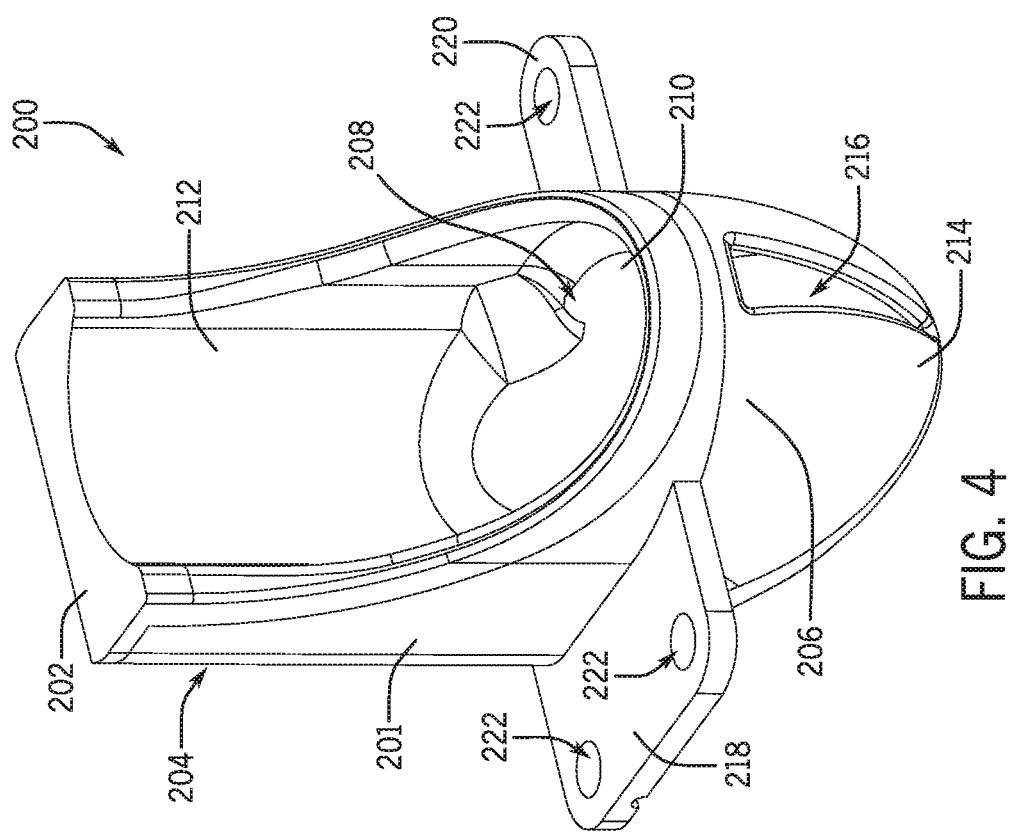
FIG. 4 is a perspective view of a handheld uroflowmeter test device that can be used with the test lab system of FIGS. 1 and 2.
Figure 6:
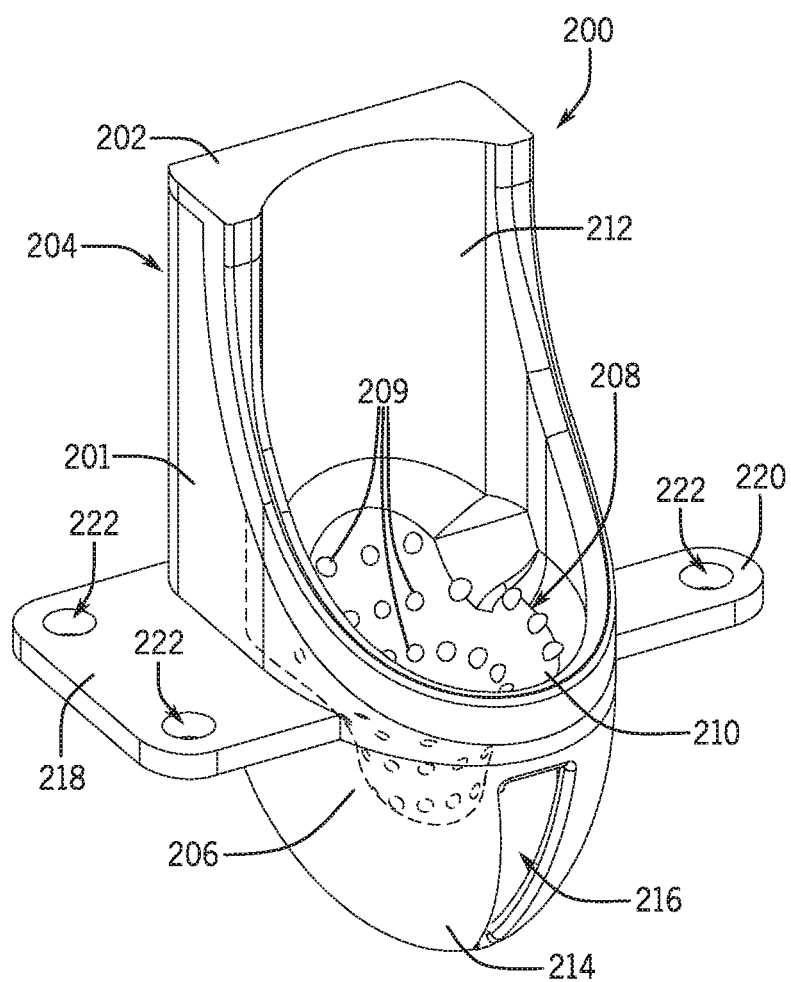
FIG. 6 is a perspective view of the handheld uroflowmeter test device of FIG. 4 including an energy dissipation feature.

With reference to FIGS. 4-7 and 12-14, test devices that may be used in the test lab system 100 of the present disclosure will now be discussed in more detail. Test devices used in the test lab system 100 may test for various shapes, materials, surfaces, and other features that may impact accurate data collection (e.g., flow rate, duration, and volume, and fluid composition). In this manner, a handheld uroflowmeter with improved data collection accuracy may be validated using the system 100 of the present disclosure. As one example, a test device may have a shape corresponding to a handheld uroflowmeter to be tested. Alternatively, the test device may be a plate to test various surface conditions. FIGS. 4-6 show a handheld uroflowmeter test device 200 that has a shape corresponding to a handheld uroflowmeter. While the handheld uroflowmeter test device 200 shown in these examples is a male model (e.g., for use by a male patient), a female model may also be used with the test lab system 100. The handheld uroflowmeter test device 200 has a main body 201 with a top surface 202, a back surface 204 and a front surface 206. The top and back surfaces 202, 204 may be generally flat surfaces. The top surface 202 may define a step or ledge 226 adjacent the back surface 204. A lower portion 205 of the back surface 204 may angle towards the front surface 206. The lower portion 205 of the back surface 204 may define a cavity 224. In one example, the cavity 224 provides a mounting location for a float-angle sensor. The front surface 206 may be a rounded surface extending from the back surface 202. The front surface 206 and the top surface 202 may define a flow chamber 208 therein. The flow chamber 208 may define a bowl 210 with a back wall 212 extending vertically therefrom. As shown in FIG. 6, the bowl 210 may include an array of vertical posts, pins, raised bumps 209 or other structures configured to dissipate the energy of a fluid stream and reduce internal turbulence that may affect flow measurement accuracy (e.g., turbulence can lead to float perturbations reducing accuracy). The front surface 206 may define a rounded bottom 214 that corresponds to the bowl 210. The rounded bottom 214 may include an outlet 216 defined therethrough that is in fluid communication with the flow chamber 208. As shown, the outlet 216 has a triangular shape that tapers towards the bottom of the uroflowmeter test device 200. While the outlet 216 depicted has a triangular shape, other shapes are contemplated to minimize turbulent flow therethrough, such as, for example, a V-shape, a T-shape, a chevron shape, a line, or a series of holes or slots with varying diameter and size. For example, a T-shape may reduce overflow at the top of the outlet 216. The uroflowmeter test device 200 may have a first and a second mounting wing 218, 220 extending from the main body 201 on opposing lateral sides. The first and second mounting wings 218, 220 may be generally flat with one or more mounting apertures 222 defined therethrough. As shown, the first wing 218 is larger than the second wing 220 and has two mounting apertures 222, while the second wing 220 has one mounting aperture 222. However, it is also contemplated that the mounting wings 218, 220 may be the same size and shape. As shown in FIG. 5, the side of the main body 201 including the second wing 220 may include an alignment tab 228 extending therefrom. The alignment tab 228 may help to position the test device 200 in a particular orientation.

Figure 7:
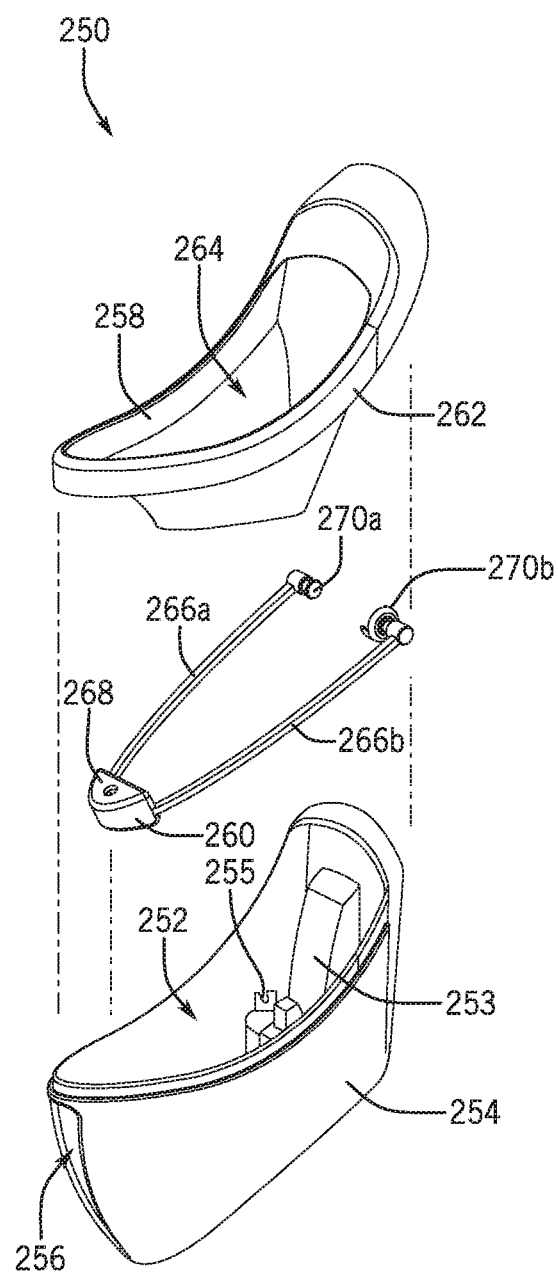
FIG. 7 is an exploded view of a handheld uroflowmeter test device that can be used with the test lab system of FIGS. 1 and 2.

FIG. 7 shows another uroflowmeter test device 250 that may be tested with the test lab system 100. The uroflowmeter test device 250 may have features similar to those discussed above for the handheld uroflowmeter test device 200. For example, the uroflowmeter test device 250 may include a flow chamber 252 surrounded by an outer wall 254 that defines an outlet 256 in fluid communication with the flow chamber 252. The outer wall 254 may include a sensor housing 253 that extends from the outer wall 254 into the flow chamber 252. The sensor housing 253 may house a device sensor. The flow chamber 252 may also house pivot support features 255. The pivot support features 255 may be coupled to the sensor housing 253 and/or the outer wall 254 inside the flow chamber 252. The uroflowmeter test device 250 may also include a funnel 258 and a float 260. For example, the funnel 258 may be coupled to the flow chamber 252. The funnel 258 may be shaped to help reduce turbulent flow and/or splash back of fluid. For example, the funnel 258 may have an outer wall 262 that has a shape corresponding to the shape of the outer wall 254 of the flow chamber 252. The funnel 258 may fit inside the flow chamber 252 such that the outer wall 262 of the funnel 258 is in contact with the outer wall 254 of the flow chamber 252. The outer wall 262 of the funnel 258 may define an aperture 264 therethrough. The aperture 264 may be in fluid communication with the outlet 256. The funnel 258 may be removable from the uroflowmeter test device 250. The funnel 258 may include a soft surface for contact with a user. The float 260 may have a plurality of arms 266a,b extending from a first end 268. The arms 266a,b may each have a pivot 270a,b at a second end. One or both of the pivots 270a,b may include a magnet. The float 260 may be positioned in an annular space defined between the outer wall 254 of the flow chamber 252 and the outer wall 262 of the funnel 258. The pivots 270a,b may pivotally couple to the outer wall 262 of the funnel 258, to the outer wall 254 of the flow chamber 252, or to both. For example, the pivots 270a,b may couple to the sensor housing 253. The pivots 270a,b may also couple to the pivot support features 255. The first end 268 of the float 260 may partially cover a lower portion of the outlet 256 to allow some fluid volume build up within the flow chamber 252 to lift the float 260. The angle and orientation of the float 260 may correspond to changes in fluid level within the uroflowmeter test device 250, such that the float 260 may be used to help measure fluid level, volume, and flow. For example, the float 260 may rise or fall in response to increases or decreases, respectively, in the level of fluid in the flow chamber 252. In some embodiments, various shapes of the funnel 258 and float 260 and the positioning of the funnel 258 and float 260 within the uroflowmeter test device 250 may be tested.

The device sensor may be housed within the sensor housing 253 and configured to detect a parameter of fluid received in the flow chamber 252. For example, the device sensor may include one or more image or optical sensors (e.g., for time of flight sensor systems), temperature sensors, inductive sensors, and/or magnetic sensors, among others. In one example, the device sensor may be an orientation sensor (e.g., an accelerometer) configured to detect the orientation of the uroflowmeter test device 250. In another example, a magnet may be positioned adjacent the device sensor, and the device sensor may be configured to detect an angular orientation of the magnet to determine a fluid level of the fluid in the flow chamber 252. In this example, the magnet may be coupled to the float 260 such that movement of the float 260 causes rotation of the magnet. For example, one or both of the float 260 pivots 270a,b may include a magnet positioned adjacent the sensor housing 253. In other examples, where the sensor is not physically isolated from the urine flow, the device sensor may be configured to detect the composition of the fluid flowing through the test device 250. For example, the device sensor may detect levels of protein, glucose, ketones, pH, and the like in urine. In yet another example, the device sensor may be a temperature sensor to determine the temperature of fluid flowing through the device 250. For example, temperature may be measured to determine whether the fluid flowing through the device 250 is a void (e.g., defined by a body temperature of about 37 degrees) or a rinse. The device sensor may be electrically coupled to the sensor 110 and/or to the computing device 240. While a few examples of sensors that can be used with the uroflowmeter test device 250 are detailed above, it is contemplated that various sensors may be used and tested within the uroflowmeter test device 250 to ensure sensor accuracy.

Figure 16:
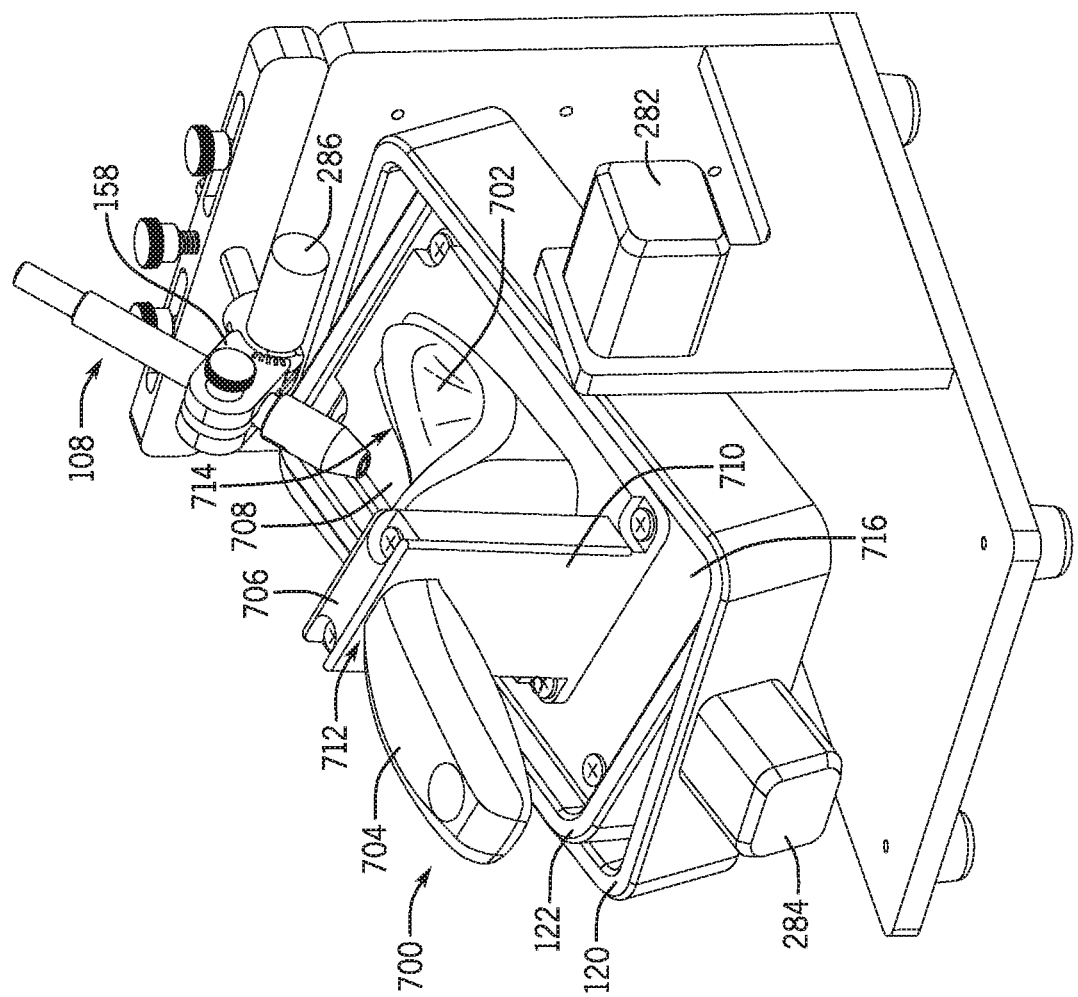
FIG. 16 is a perspective view of the motorized test flow bench of FIG. 15 with a test device.

FIG. 16 shows another uroflowmeter test device 700 that may be tested with the test lab system 100. The uroflowmeter test device 700 may include similar features as the uroflowmeter test device 200. For example, the uroflowmeter test device 700 may include a bowl 702. The uroflowmeter test device 700 may also include a handle 704. The handle 704 may include a feedback device providing feedback to a user relating to the angle and/or orientation of the uroflowmeter test device 700. For example, the feedback device may be a light that flashes different colors depending on the angle of the uroflowmeter test device 700. For example, a green light may indicate a proper angle for the uroflowmeter test device 700 (e.g., an angle producing accurate flow measurements).

As shown in FIG. 16, the test lab system 100 may include a stabilizing body 706 that couples to the uroflowmeter test device 700. The stabilizing body 706 may have a horizontal plate 708 coupled to a vertical plate 710. The vertical plate 710 may form a backing. The vertical plate 710 may include a handle aperture 712 for receiving the handle 704 of the uroflowmeter test device 700. The horizontal plate 708 may include a bowl aperture 714 for receiving the bowl 702 of the uroflowmeter test device 700. The stabilizing body 706 may be coupled to the mounting frame 122 of the frame assembly 106. The stabilizing body 706 may be coupled to the mounting frame 122 directly or via a plate 716 (e.g., as shown in FIG. 16). As shown, the stabilizing body 706 may hold the uroflowmeter test device 700 in an upright position (e.g., at a 90 degree angle to the mounting frame 122), preventing the uroflowmeter test device 700 from accidentally tipping over on a side during testing of the uroflowmeter test device 700.

Figure 12:
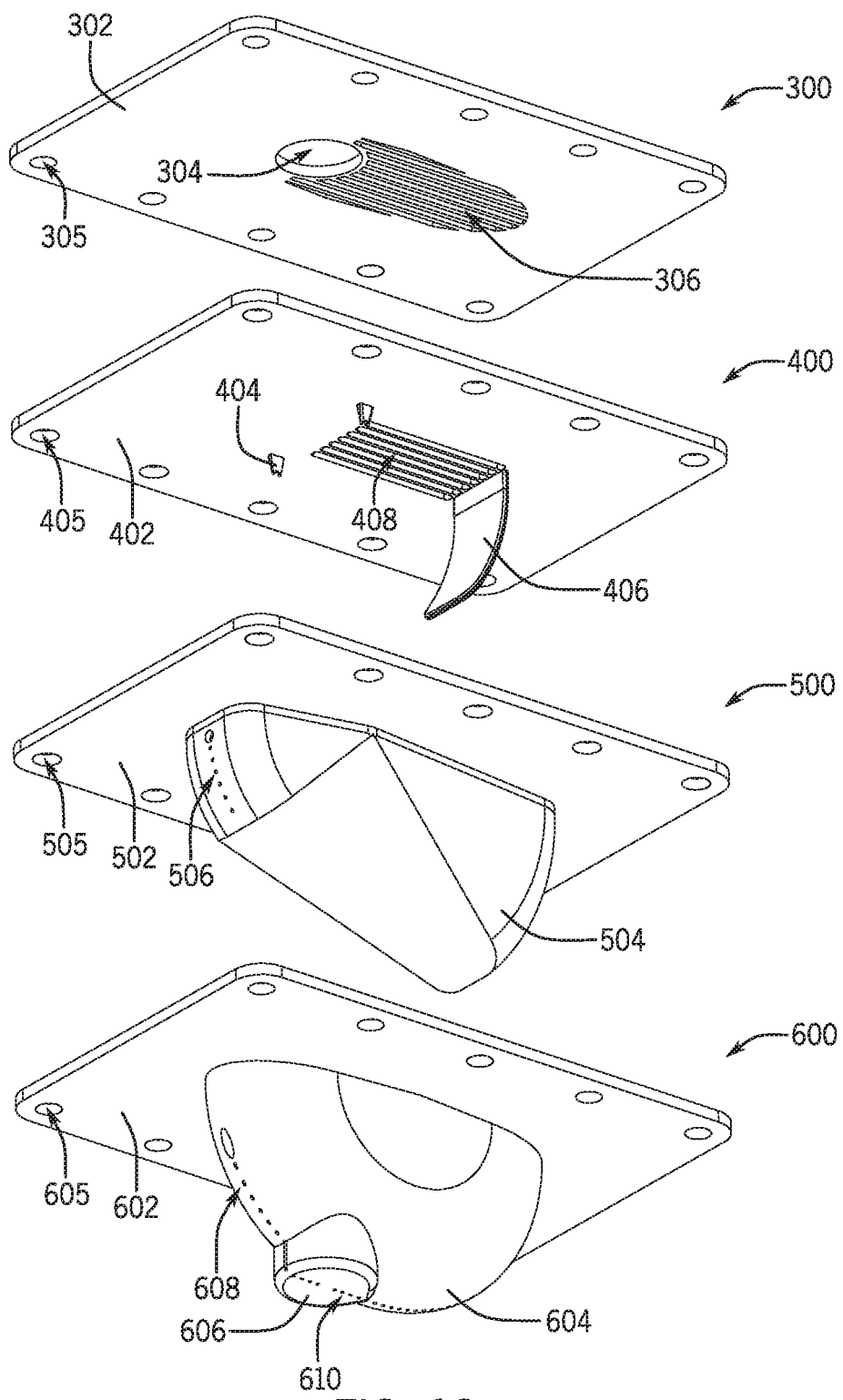
FIG. 12 is a perspective view of various surface test devices that can be used with the test lab system of FIGS. 1 and 2.

FIG. 12 shows various surface test devices 300, 400, 500, 600 to test various surface conditions, textures, features, and float technology. The surface test devices 300, 400, 500, 600 may be plates defining various apertures and with various shapes and cavities extending therefrom. The features on the surfaces of the various surface test devices 300, 400, 500, 600 may absorb, deflect or diffuse urine stream energy. Such features can be tested, for example, for the ability to reduce or prevent temporary effects on a float associated with a handheld uroflowmeter as well as potential splash back on a user. As one example, different orientations and shapes of grating may be tested for their abilities to dissipate urine stream energy. For example, the surface test device 300 may be used to explore dissipating urine stream energy. The surface test device 300 may have a flat surface 302 with a central aperture 304 and a grate 306. Different grating may be tested with surface test device 300 for its ability to dissipate energy of a urine stream. In application, the grate 306 may be included with a handheld uroflowmeter having a shape similar to that of the uroflowmeter test device 200, and the grate 306 may be recessed relative to the upper surface of an inlet to the flow chamber 208 to limit urine splash back. As another example, the surface test device 400 may have a flat bottom surface 402 with pegs or float pivot supports 404 and a curved wall or guard 406 extending therefrom. The surface 402 may also define a grate 408 that is adjacent to the curved wall 406. Such a surface test device 400 may be used to test urine deflection. For example, a float may be positioned near the convex side of the curved wall 406, and the curved wall 406 may deflect a urine stream away from the float to reduce the chance that the power of the urine stream might affect float action.

Figure 13:
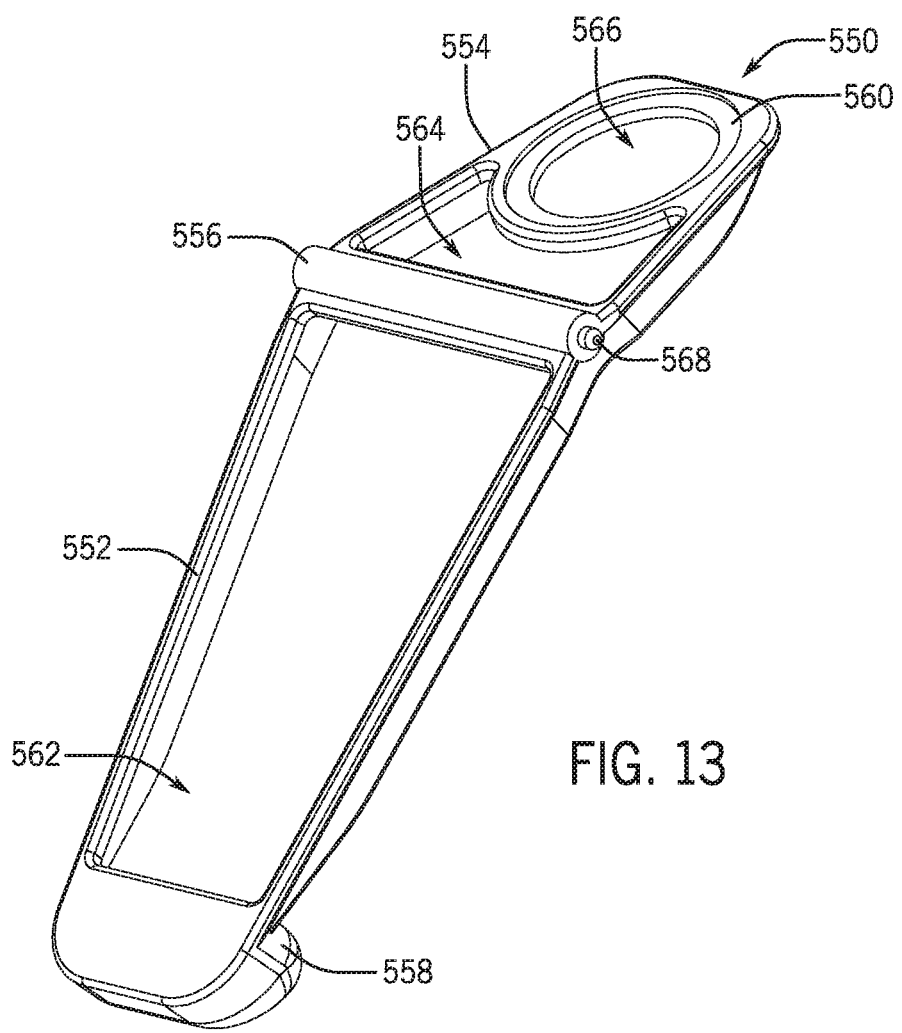
FIG. 13 is a perspective view of a float that can be used with a test device of FIG. 12.
Figure 14:
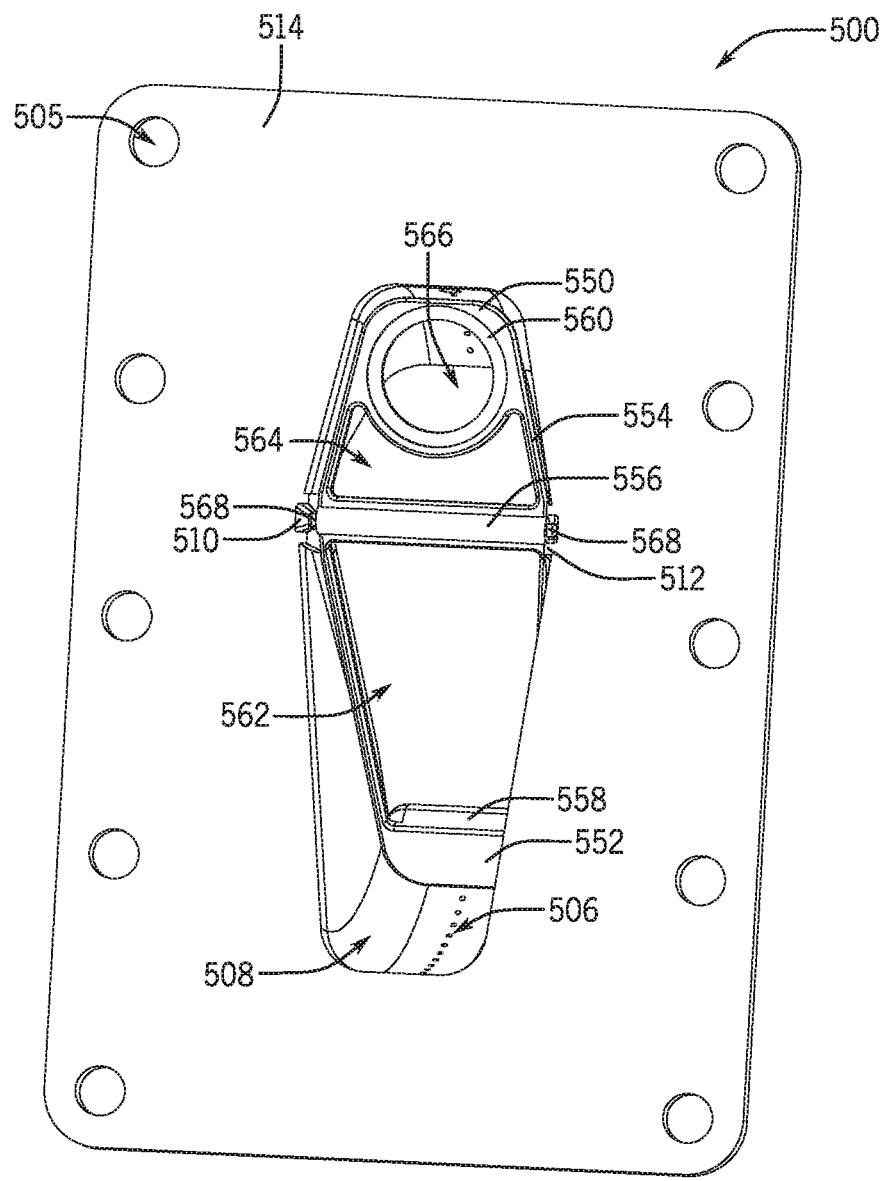
FIG. 14 is a perspective view of the float of FIG. 13 in a test device of FIG. 12.

Other test devices may test for various features related to detecting a more accurate flow rate. For example, various shapes and orientations of an outlet may be tested to provide a known exit flow rate based on the urine level in, and the orientation of, a flow chamber. The optimal shape and orientation of the outlet may also vary with different float shapes. In this manner, different float shapes may be tested with various test devices having different outlets. In one example, as shown in FIGS. 12-14, a surface test device 500 may be used to test an exit hole pattern consisting of several apertures 506, as opposed to the V-shaped outlet 216 of the uroflowmeter test device 200. The surface test device 500 may have a flat bottom surface 502 and top surface 514, with a partially spherical bowl 504 extending from the bottom surface 502. The bowl 504 may define a plurality of apertures 506 on an upper portion of an outer surface. In one example, the exit hole pattern of the surface test device 500 may be tested with the float 550 shown in FIG. 13. As shown in FIG. 13, the float 550 may have a first arm 552 and a second arm 554 that are offset at an angle relative to one another. The two arms 552, 554 may intersect at an axle 556. As shown, the axle 556 is offset from the center, such that the first arm 552 is longer than the second arm 554; however, it is contemplated that the axle 556 may be closer to the center of the float 550. The axle 556 may include two knobs or pivots 568 on opposing ends. The first arm 552 may include a bottom lip 558 that extends outwards from the end opposite the axle 556. The second arm 554 may include a ring 560 on the end opposite the axle 556. The arms 552, 554 may define one or more central apertures. For example, the first arm 552 may define a central aperture 562, and the second arm 554 may define a first central aperture 564 and a second central aperture 566. As shown, the second central aperture 566 has a generally circular shape defined by the ring 560. The ring 560 and the second central aperture 566 are configured to hold a sensor-target (e.g., a metal sensor-target) within the float 550. The float 550 may be shaped to reduce travel of the second arm 554 (e.g., containing the metal sensor-target) and to reduce exposure of the second arm 554 (and of the metal sensor-target if contained therein) to urine.

As shown in FIG. 14, the float 550 may be positioned within the bowl 504. The bowl 504 may define a cavity 508 configured to receive the float 550. For example, the bowl 504 may include tracks 510, 512 on opposing sides. The tracks 510, 512 may receive the knobs 568 on either end of the float 550, pivotally coupling the float 550 to the surface test device 500. As shown, when the float 550 is positioned within the cavity 508, the first arm 552 may extend down into the cavity 508, while the second arm 554 may be flush with the top surface 514 of the surface test device 500. The positioning of the knobs 568 inside of the tracks 510, 512 allows the float 550 to rotate about the axle 556 in the cavity 508. In operation, when the surface test device 500 is mounted on the test flow bench 102, fluid may be directed into the bowl 504. As the fluid fills the bowl 504, the first arm 552 may rise up towards the top surface 514, causing the axle 556 to rotate within the tracks 510, 512, and the second arm 554 to lower within the cavity 508. The rate the float 550 rotates may vary depending upon the size of the central apertures 562, 564, 566 on the float 550 as well as the size and number of the apertures 506 on the bowl 504. An extension 558 of the float 550 may extend below the first arm 552 to allow the float shape to more closely match the internal geometry of the bowl 504. The movement of the float 550 may correlate to fluid flow through the device 500 and may be measured using a device sensor.

Different shaped test devices may be ideal for testing various float shapes. For example, as shown in FIG. 12, a surface test device 600 may be used to test a ring or disk-shaped float. The surface test device 600 may include a flat bottom surface 602 with a half-spherical bowl or tire shape 604 extending therefrom. The half-spherical bowl or tire shape may be less susceptible to user-induced angle errors. The half-spherical bowl 604 may have a partially cylindrical feature 606 extending therefrom. The half-spherical bowl 604 may define a plurality of apertures 608 around a lower portion of an outer periphery, and the partially cylindrical feature 606 may define a plurality of apertures 610 on its lower surface that align with the apertures 608 on the half-spherical bowl 604, forming a line of both apertures 608, 610. A ring or disk-shaped float and a device sensor may be positioned within a chamber defined by the half-spherical bowl 604 and partially cylindrical feature 606. The disk-shaped float may have a metal top surface. The disk-shaped float may move vertically within the partially cylindrical feature 606 as fluid builds within the chamber, and the device sensor may measure the distance to the metal surface. By measuring the movement distance of the float, fluid flow through the surface test device 600 can be calculated.

The surface test devices 300, 400, 500, 600 shown each have a generally rectangular shaped plate; however, other shapes are contemplated. Each surface test device 300, 400, 500, 600 has mounting apertures 305, 405, 505, 605 on opposing edges for mounting the device to the test flow bench 102.

The one or more test devices 200, 250, 300, 400, 500, 600 may be selectively mounted to the test flow bench 102 to test simulated urine flow onto each device. For example, as shown in FIGS. 8 and 9, the uroflowmeter test device 200 may be coupled to the frame assembly 106. More specifically, the uroflowmeter test device 200 may be coupled to the mounting frame 122. The uroflowmeter test device 200 may be placed such that the wings 218, 220 are positioned on top of the mounting surface 132 and the mounting apertures 222 align with the one or more mounting apertures 138 on the mounting surface 132. One or more fasteners 144 may be positioned through the apertures 222, 138 to couple the uroflowmeter test device 200 to the mounting frame 122. In this manner, the main body 201 of the uroflowmeter test device 200 is positioned within the central opening 140 of the mounting frame 122 and is suspended above the base plate 112. The uroflowmeter test device 200 may be positioned on the mounting frame 122 such that the main body 201 and flow chamber 208 are below the adjustable nozzle 108. In a similar manner, the other test devices 300, 400, 500, 600 may be mounted to the test flow bench 102 by aligning the mounting apertures 305, 405, 505, 605 with the one or more mounting apertures 138 on the mounting surface 132 and positioning the one or more fasteners 144 through the apertures 305, 405, 505, 605 and 138 to couple the surface test devices 300, 400, 500, 600 to the mounting frame 122, such that the surface test devices 300, 400, 500, 600 seat within the central opening 140.

The test flow bench 102 may be in communication with a computing device 240 to adjust parameters and components associated with the one or more test devices 200, 250, 300, 400, 500, 600. For example, the computing device 240 may be in communication with the sensor 110, with a device sensor within the test device 200, 250, 300, 400, 500, 600, and/or with the pump 113. The computing device 240 may be, for example, a computer server, a mainframe computer, a distributed computer, a personal computer (PC), a workstation connected to a central computer or server, a notebook or portable computer, a tablet PC, a smart phone device, an Internet appliance, or other computer devices, or combinations thereof, with internal processing and memory components, a user interface, as well as interface components for connection with external input, output, storage, network, and other types of peripheral devices. The computing device 240 may perform various functions within the test lab system 100. For example, the computing device 240 may control various flow parameters (e.g., flow rate, duration, volume, and the like) and may control the angle and orientation of various test flow bench components. The computing device 240 may be in communication with an external database to gather real world data on urine flow profiles under real conditions. With real world data, the computing device 240 may adjust parameters within the test lab system 100 to simulate real world conditions. For example, the computing device 240 may adjust fluid velocity or flow rate through the pump 113 to match a realistic urine velocity or flow rate based on the accumulated real world data.

In operation, the test lab system 100 may be used to test various test devices, such as, for example, the test devices 200, 250, 300, 400, 500, 600 discussed herein, for their performance capabilities. For example, the test lab system 100 may be used to design and improve a handheld uroflowmeter of the present disclosure. As one example, an exemplary uroflowmeter may be generated on a 3D printer, fitted with exemplary level sensors, and placed within the test flow bench 102. Once a test device 200, 250, 300, 400, 500, 600 is mounted to the test flow bench 102 and positioned beneath the adjustable nozzle 108, the adjustable nozzle 108 may be used to test fluid flow (simulating urine flow) on the test device 200, 250, 300, 400, 500, 600. Fluid may be pumped from the pump 113 through the fluid supply tubing 188 to the adjustable nozzle 108. For example, the computing device 240 may be used to control the pump controller 115 and subsequently the pump 113 and thus fluid flow through the adjustable nozzle 108. The desired fluid flow rate may be set via the pump controller 115 to produce fluid flow out the pump 113 at an expected flow rate. Fluid flows through the fluid supply tubing 188, through the tube-receiving aperture 111 in the sensor 110, into the cavity 156 defined within the body 150 of the adjustable nozzle 108, out the first end 152, and onto the test device 200, 250, 300, 400, 500, 600 positioned below. For example, when fluid flows onto the uroflowmeter test device 200, it enters the flow chamber 208 and exits the flow chamber through the outlet 216. After fluid flows through the test device 200, 250, 300, 400, 500, 600, it may be funneled into outflow tubing 189 that is coupled to the pump 113. In this manner, the fluid flows back into the pump 113 where it can be recycled back into the system 100.

As the fluid flows through (or adjacent) the sensor 110, the sensor 110 can measure the actual flow rate of fluid flowing therethrough. This actual flow rate can be compared to the expected flow rate (produced at the pump 113), and the flow rate at the pump 113 can be adjusted to account for any variation in order to produce an actual flow rate that is the same, or substantially the same, as the expected flow rate. In other embodiments, the sensor 110 may detect various flow characteristics, such as duration, volume, timestamp of the void and/or other parameters. In an alternative arrangement having a different architecture for the plates, the sensor 110 may also detect the orientation angle of the device 200, 250, 300, 400, 500, 600 and/or the adjustable nozzle 108. The sensor 110 may transmit the collected data to the computing device 240 for additional processing. As one example, the computing device 240 may have stored information on optimal flow parameters. The computing device 240 may compare the collected data to the stored data to determine any offset from the optimal flow parameters, such that a user can make adjustments to optimize the results. In this manner, the data may be used to determine an optimal structure for a handheld uroflowmeter of the present disclosure.

The angle, positioning, and distance of a fluid stream onto the test device 200, 250, 300, 400, 500, 600 may be varied by adjusting one or more components on the test flow bench 102. For example, the pitch, roll, xz/yz planes, and/or lateral motion of various components may be adjusted. As one example, as shown in FIGS. 10A-B and 11A-B, the frame assembly 106 may be adjusted for orientation angle (pitch/roll, or xz/yz planes) via the tilt control knob 148 or roll control knob 142.

Figure 10A:
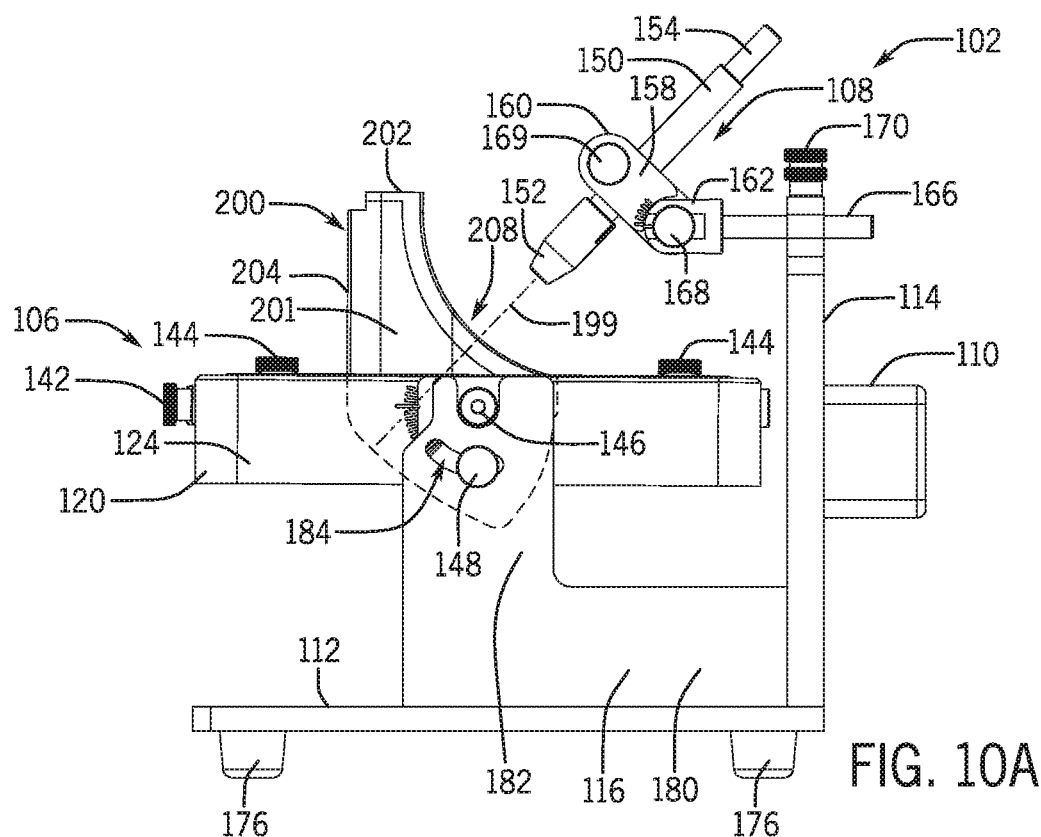
FIG. 10A is a side view of the test flow bench and the handheld uroflowmeter test device of FIG. 8 showing fluid flow when the test flow bench is in a first configuration.
Figure 10B:
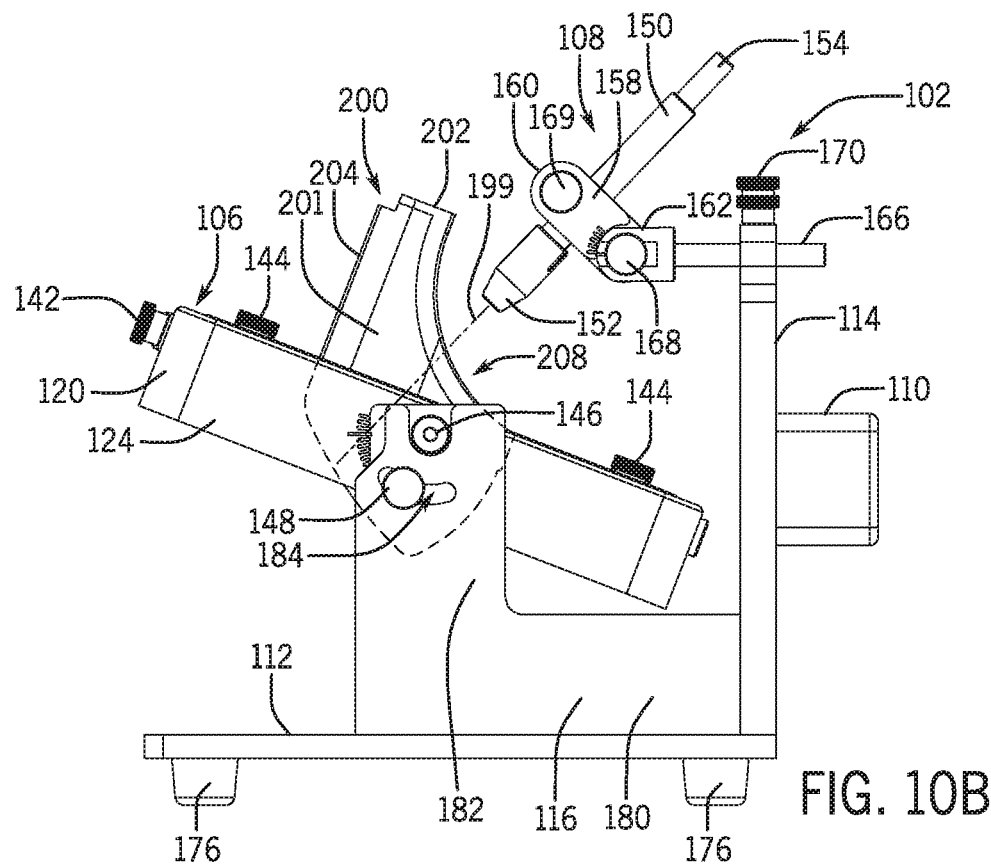
FIG. 10B is a side view of the test flow bench and the handheld uroflowmeter test device of FIG. 8 showing fluid flow when the test flow bench is in a second configuration.

With reference to FIGS. 10A-B, the tilt control knob 148 may be moved within the tilt control slot 184 to adjust the pitch of the frame assembly 106. For example, the tilt control knob 148 may be slid or rotated to reposition the tilt control knob 148 within the tilt control slot 184. Movement of the tilt control knob 148 simultaneously moves the support frame 120 and the mounting frame 122. This movement of the frame assembly 106 in turn moves the uroflowmeter test device 200. As shown in FIG. 10A, when the tilt control knob 148 is in a first position, the frame assembly 106 may have a flat orientation (e.g., parallel to the base plate 112), and the fluid path 199 may strike more center or more towards the back wall 212 of the uroflowmeter test device 200, depending also upon the positioning of the adjustable nozzle 108. When the tilt control knob 148 is moved upwards through the tilt control slot 184, in a direction away from the back plate 114, the frame assembly 106 may tilt in a direction towards the back plate 114. In other words, the top surface 126 of the support frame 120 and the mounting surface 132 of the mounting frame 122 angle towards the back plate 114. In this example, the uroflowmeter test device 200 may be angled such that the top surface 202 tilts towards the back plate 114. FIG. 10B shows the tilt control knob 148 in a second position with the frame assembly 106 and uroflowmeter test device 200 angled towards the back plate 114. In this position, the fluid path 199 may strike the bowl 210 of the flow chamber 208 more directly (e.g., with less fluid hitting the back wall 212), depending again on the angle of the adjustable nozzle 108 as well.

Figure 11A:
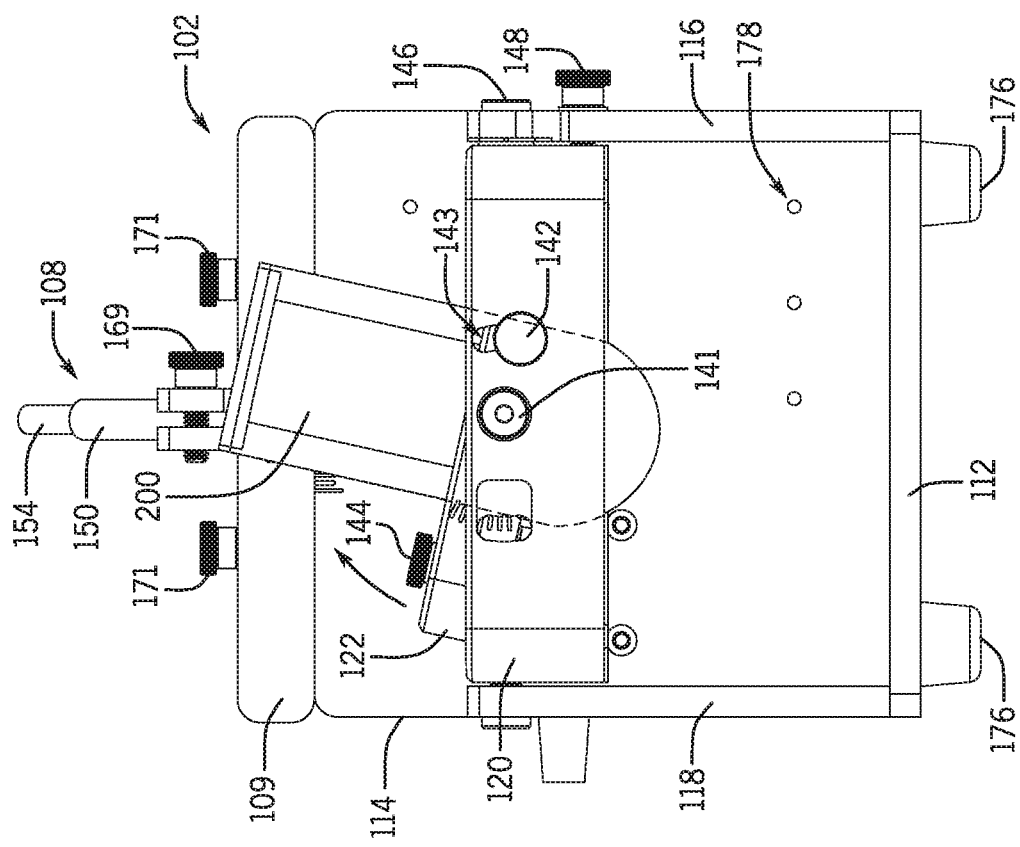
FIG. 11A is a front view of the test flow bench and the handheld uroflowmeter test device of FIG. 8 showing roll of a mounting frame of the test flow bench in a first direction.
Figure 11B:
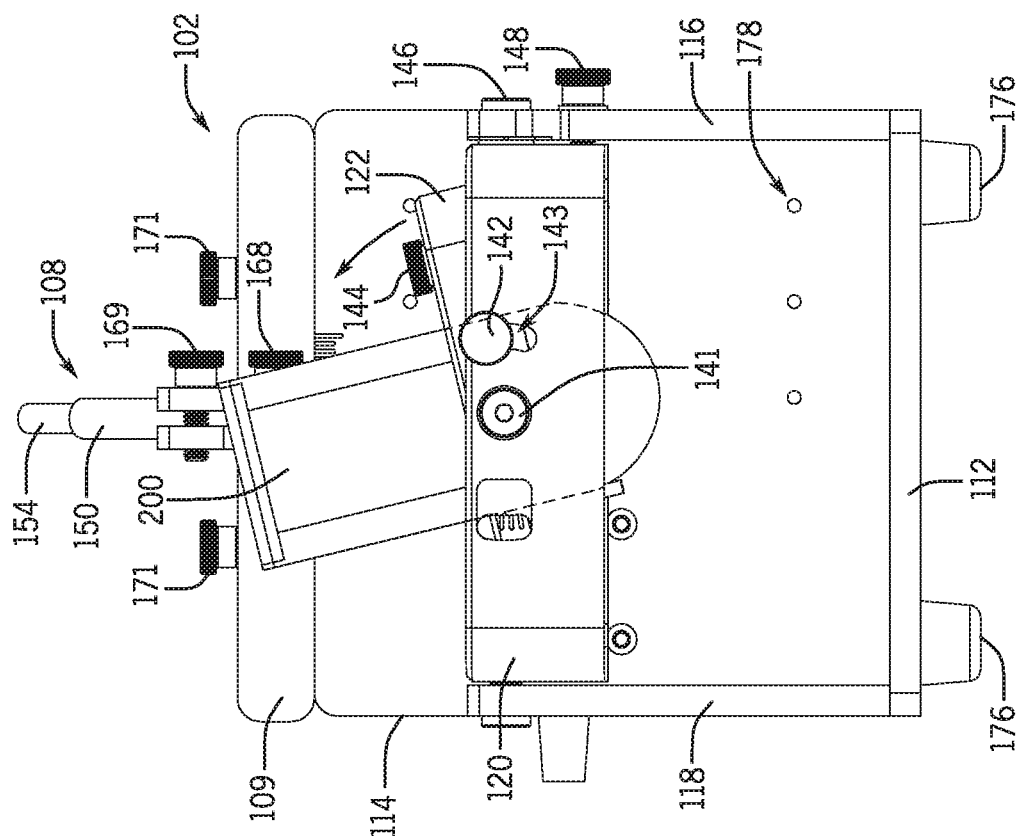
FIG. 11B is a front view of the test flow bench and the handheld uroflowmeter test device of FIG. 8 showing roll of the mounting frame in a second direction.

As shown in FIGS. 11A-B, the roll control knob 142 may be repositioned within the roll control slot 143 to adjust the roll of the mounting frame 122. For example, the roll control knob 142 may be slid or rotated to reposition the roll control knob 142 within the roll control slot 143. Movement of the roll control knob 142 simultaneously rotates the mounting frame 122 relative to the support frame 120. This movement of the mounting frame 122 in turn moves the uroflowmeter test device 200. As shown in FIG. 11A, when the roll control knob 142 is in a first position, the mounting frame 122 may rotate in a direction towards the second arm 118. As shown in FIG. 11B, when the roll control knob 142 is in a second position, the mounting frame 122 may rotate in a direction towards the first arm 116. Movement of the uroflowmeter test device 200 in this manner may result in the fluid path striking more towards either sidewall of the bowl 210 than directly center into the bowl 210. Such variation may allow a tester to simulate a user holding the handheld uroflowmeter off-center and to test for splash back under such conditions. Thus, by adjusting the position of the frame assembly 106, the path of fluid flow on the uroflowmeter test device 200 may be varied.

As another example, the path of fluid flow on the uroflowmeter test device 200 may also be varied by adjusting the adjustable nozzle 108. For example, the adjustable nozzle 108 may be adjusted for inflow angle, position, and stream shape. The angle of the adjustable nozzle 108 may be adjusted via the angle adjustment knob 168 on the adjustable mounting body 158 or the position of the adjustable nozzle 108 may be adjusted by moving the adjustable nozzle 108 either laterally or longitudinally. As one example, the angle adjustment knob 168 may be rotated to change the angle of the first end 160 of the adjustable mounting body 158 relative to the second end 162. Adjusting the angle of the first end 160, adjusts the angle of the body 150 and the direction that fluid flows therethrough. The adjustable nozzle 108 may be angled such that fluid flows directly onto the bowl 210, the back wall 212, or somewhere in between on the uroflowmeter test device 200. As another example, the axial adjustment knob 169 may be rotated to loosen the grip of the adjustable mounting body 158 on the adjustable nozzle body 150, and the adjustable nozzle body 150 may be repositioned axially within the adjustable mounting body 158. In this manner the adjustable nozzle body 150 may be repositioned closer to or further away from the uroflowmeter test device 200. Such an adjustment may be beneficial for testing different distances that a user may hold the uroflowmeter relative to the user's body.

The position of the adjustable nozzle 108 may also be adjusted relative to the support assembly 104. As one example, the adjustable nozzle 108 may be repositioned longitudinally relative to the back plate 114. The rod fastener 170 may be loosened within the nozzle fastening aperture 117 to allow for axial movement of the rod 166 within the nozzle receiving aperture 175 defined within the adjustable upper portion 109 of the back plate 114. With reference to FIG. 8, such movement of the adjustable nozzle 108 may position the first end 152 closer to either the front surface 206 or the back surface 204 of the test device 200. As another example, the adjustable nozzle 108 may be repositioned laterally. The fasteners 171 may be loosened within the lateral adjustment slots 173 and the adjustable upper portion 109 may be slid laterally, changing the position of the fasteners 171 within the lateral adjustment slots 173. Lateral movement of the upper portion 109 moves the adjustable nozzle 108 laterally. With reference to FIG. 8, such movement of the adjustable nozzle 108 may position the first end 152 closer to either side surface of the test device 200.

Figure 15:
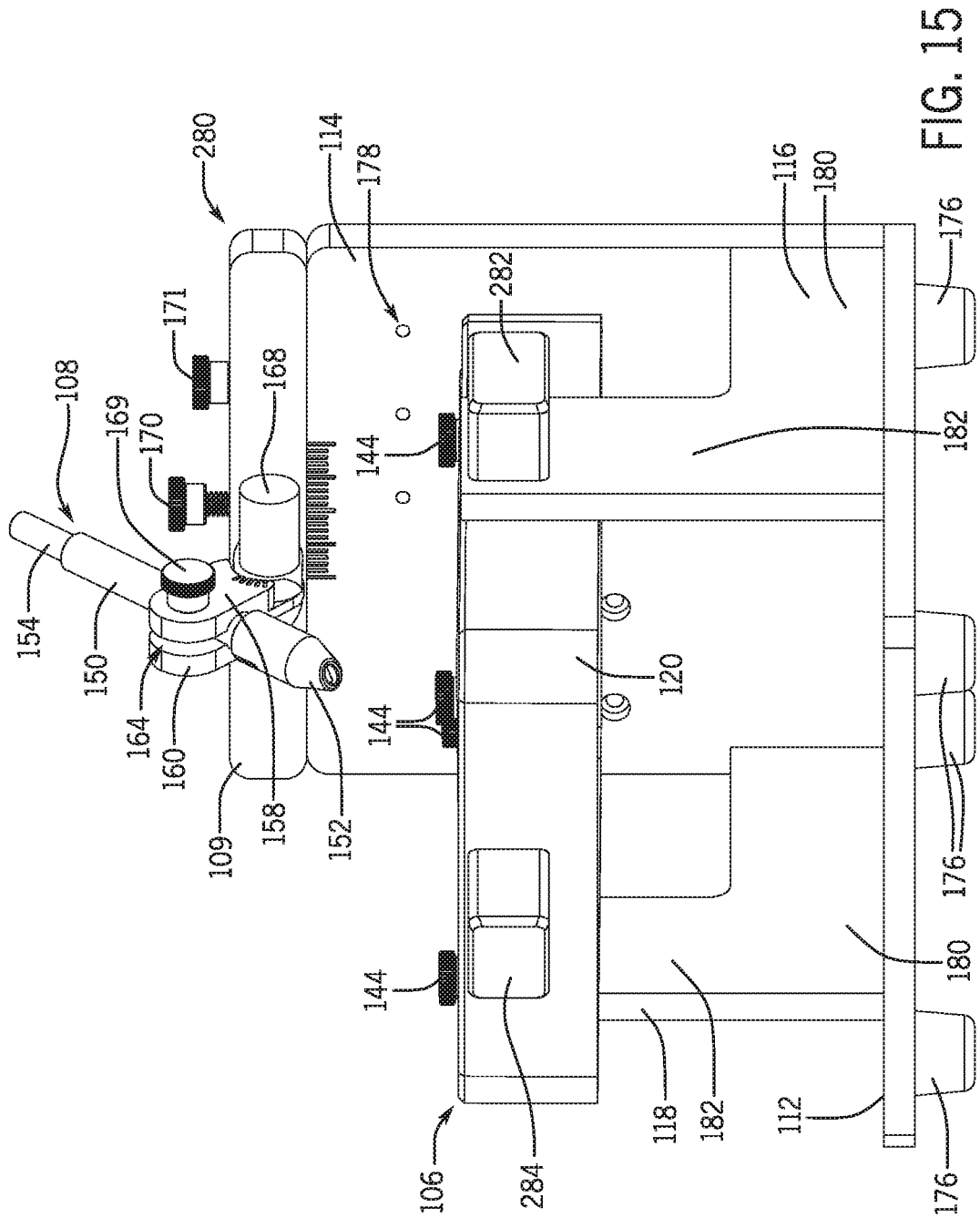
FIG. 15 is a perspective view of a motorized test flow bench that can be used with the test lab system of FIGS. 1 and 2.

In an alternate embodiment, as shown in FIGS. 15 and 16, the system 100 may include a motorized test flow bench 280. The motorized test flow bench 280 may include many of the same features as the manual test flow bench 102. However, instead of knobs 168, 142, 148 to control nozzle angle and frame assembly roll and pitch, the motorized test flow bench 280 may include one or more motors (e.g., servomotors). As shown, the motorized test flow bench 280 may include a nozzle adjustment motor 286, a tilt or pitch control motor 282, and a roll control motor 284. The nozzle adjustment motor 286 may be used to adjust the angle and/or positioning of the adjustable nozzle 108 relative to a test device positioned on the motorized test flow bench 280, while the tilt control motor 282 and roll control motor 284 may be used to adjust the orientation, angle, pitch and/or roll of a test device relative to the adjustable nozzle 108. The nozzle adjustment motor 286 may be coupled to the adjustable mounting body 158 and adjustable nozzle 108, the tilt control motor 282 may be coupled to the support frame 120, and the roll control motor 284 may be coupled to an arm 116, 118 of the support assembly 104 and to the mounting frame 122. Each motor 282, 284, 286 may be coupled to the computing device 240 (e.g., directly or wirelessly), which can be used to activate and control the motors 282, 284, 286. The adjustable nozzle 108 angle and/or positioning may be adjusted by activating the nozzle adjustment motor 286, and the frame assembly 106 pitch and roll may be adjusted by activating the tilt control motor 282 and the roll control motor 284, respectively. While three motors are depicted, it is contemplated that any number of motors may be used. For example, one motor may be used to control both pitch and roll of the frame assembly 106. The nozzle adjustment motor 286 may allow for a greater range of motion of the adjustable nozzle and the tilt and roll control motors 282, 284 may allow for a greater range of motion for the frame assembly 106 than the manual flow test bench 102 depicted in FIGS. 1-3 and 8-11B. For example, the range of motion of the manual test flow bench 102 may be limited by the size of the tilt control slot 184 and/or the roll control slot 143. However, the motors 282, 284 are not so limited and may rotate the support frame 120 and/or mounting frame 122 with an increased range of motion.

The motors 282, 284, 286 may allow precise, repeatable and programmed movement of the respective frame assembly 106 and adjustable nozzle 108. In this manner, movement can be tracked between tests in order to capture flow data related to the manner in which flow results change with device angle, pitch, and/or roll. The motors 282, 284, 286 each have an axis that may use a sensor (e.g., an optical slot sensor) for homing. A relative position encoder on each motor 282, 284, 286 may be used for position feedback once home is known. Any conventional encoder may be used with the motors 282, 284, 286. In this manner, the positioning of the adjustable nozzle and/or any test device used with the motorized test flow bench 280 may be easily determined and/or adjusted with each test run.

In either the manual or motorized test flow bench embodiments, adjusting the position of the frame assembly 106 simulates the different angles that a user may hold a handheld uroflowmeter. Adjusting the position of the adjustable nozzle 108 simulates different angles that urine may exit a person. For example, the angle may vary depending upon whether the person is male or female. Thus, the angle may be adjusted depending upon whether a male version or female version of a handheld uroflowmeter is being tested to obtain more accurate results. As one example, a male version test device may have a flow chamber with a vertical backstop to direct or guide a user's urine into a bowl of the flow chamber. With such a device, the adjustable nozzle 108 may be positioned to direct the urine stream more towards the backstop than directly into the bowl, in order to replicate a typical male user's urine stream orientation. By adjusting the positioning of a uroflowmeter test device and the adjustable nozzle 108 during testing, a tester can improve the design of the uroflowmeter test device to better accommodate user interaction with the device and optimize the device's measuring capabilities.

By directing fluid to different positions within the flow chamber 208 of the device 200, the structure of the flow chamber 208 can be tested for its capacity for fluid flow therethrough. For example, the volume of fluid that flows through the flow chamber 208, the amount of fluid splash back, any turbulence in the fluid flow, the amount of fluid build-up within the flow chamber 208, the amount of fluid overflow out the flow chamber 208, the rate of fluid flow through the flow chamber 208, and the like may be measured with the device 200 at different angles. The shape of the device 200 may be adjusted to obtain better fluid flow through the device (e.g., less fluid splash back, turbulence, build-up, and/or overflow) that is less impacted by varying angles and orientation.

All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the structures disclosed herein, and do not create limitations, particularly as to the position, orientation, or use of such structures. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. The exemplary drawings are for purposes of illustration only and the dimensions, positions, order and relative sizes reflected in the drawings attached hereto may vary.

The above specification, examples and data provide a complete description of the structure and use of exemplary embodiments of the invention as defined in the claims. Although various embodiments of the claimed invention have been described above with a certain degree of particularity, or with reference to one or more individual embodiments, those skilled in the art could make numerous alterations to the disclosed embodiments without departing from the spirit or scope of the claimed invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A test lab system for testing and validating a uroflowmeter, comprising:
   a test flow bench configured to test fluid flow through a test device, comprising:
      a support assembly;
      a frame assembly pivotally coupled to the support assembly and configured to support the test device;
      an adjustable nozzle coupled to the support assembly and positioned above the frame assembly;
      a sensor coupled to the support assembly; and
      one or more motors in electrical communication with a computing device and configured to control pitch and roll of the frame assembly relative to the support assembly.

2. The test lab system of claim 1, wherein the support assembly comprises:
   a base plate;
   a back plate orthogonally coupled to the base plate; and
   two arms coupled to opposing side edges of the base plate, wherein at least one of the two arms defines a tilt control slot for receiving a tilt control knob to pivotally couple the frame assembly to the at least one arm.

3. The test lab system of claim 2, wherein the adjustable nozzle is coupled to an adjustable upper portion of the back plate, wherein lateral movement of the adjustable upper portion moves the adjustable nozzle in a lateral direction.

4. The test lab system of claim 2, further comprising the test device coupled to the frame assembly, wherein movement of the tilt control knob within the tilt control slot pivots the frame assembly and the test device, moving the test device from a first position to at least a second position.

5. The test lab system of claim 4, wherein fluid flowing through the adjustable nozzle strikes a first surface of the test device when the test device is in the first position and a second surface of the test device when the test device is in the second position.

6. The test lab system of claim 1, further comprising the test device, wherein the frame assembly comprises a mounting frame pivotally coupled to a support frame, and the test device is coupled to the mounting frame, wherein roll of the mounting frame relative to the support frame alters a roll angle of the test device.

7. The test lab system of claim 1, wherein the adjustable nozzle is adjustable in at least one of an angular, axial, or lateral direction.

8. The test lab system of claim 1, further comprising the test device coupled to the frame assembly, wherein the test device comprises a main body defining a flow chamber, wherein the flow chamber comprises a concave surface defining an outlet with a back wall extending vertically from the concave surface.

9. The test lab system of claim 8, wherein the shape of the test device is tested for impact on one or more fluid flow parameters of fluid flowing through the test device, the fluid flow parameters comprising at least one of fluid flow rate, duration, volume, overflow, splash back, and turbulence.

10. The test lab system of claim 8, wherein the adjustable nozzle is coupled to a fluid source, wherein movement of the adjustable nozzle adjusts a path of fluid flow onto the test device when fluid is pumped through the adjustable nozzle.

11. The test lab system of claim 1, wherein the sensor is configured to detect actual flow rate of fluid flowing through the adjustable nozzle.

12. A method of testing and developing a uroflowmeter, comprising:
   mounting a test device to a test flow bench, wherein the test flow bench comprises:
      a support assembly;
      a frame assembly pivotally coupled to the support assembly;
      an adjustable nozzle coupled to the support assembly and to a fluid source; and
      a sensor coupled to the support assembly; wherein the test flow bench is electrically coupled to a computing device; and
      the test device is configured to test one or more features of a uroflowmeter;
   adjusting the frame assembly, the adjustable nozzle, or both;
   pumping fluid from the fluid source through the adjustable nozzle to the test device;
   monitoring, by the computing device, at least one fluid flow parameter of the fluid flowing through the test device, wherein the at least one fluid flow parameter is detected by the sensor and data related to the at least one fluid flow parameter is transmitted to the computing device; and
   adjusting the test device based on the at least one detected fluid flow parameter and a desired fluid flow parameter.

13. The method of claim 12, wherein the one or more features of the uroflowmeter comprise at least one of device shape and size, outlet shape and size, one or more surface features, and float shape and positioning within the uroflowmeter.

14. The method of claim 12, wherein the at least one fluid flow parameter comprises at least one of fluid flow rate, volume, duration, overflow, turbulence, splash back, and timestamp.

15. The method of claim 12, wherein the test device is a plate configured to test a surface feature of the uroflowmeter, wherein the surface feature is at least one of surface shape, grating, protruding features, and aperture number, size and positioning.

* * * * *